(12) United States Patent
Kokubo et al.

(10) Patent No.: US 11,324,454 B2
(45) Date of Patent: May 10, 2022

(54) BLOOD PRESSURE MEASUREMENT APPARATUS, METHOD OF CONTROLLING BLOOD PRESSURE MEASUREMENT APPARATUS, AND PROGRAM

(71) Applicant: OMRON HEALTHCARE CO., LTD., Kyoto (JP)

(72) Inventors: Ayako Kokubo, Kyoto (JP); Hirotaka Wada, Kyoto (JP); Eriko Kan, Kyoto (JP); Keiichi Obayashi, Kyoto (JP); Masaaki Kasai, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 464 days.

(21) Appl. No.: 16/281,212

(22) Filed: Feb. 21, 2019

(65) Prior Publication Data

US 2019/0209096 A1      Jul. 11, 2019

Related U.S. Application Data

(63) Continuation of application No. PCT/JP2017/031862, filed on Sep. 5, 2017.

(30) Foreign Application Priority Data

Sep. 12, 2016    (JP) .............................. JP2016-177704

(51) Int. Cl.
*A61B 5/00*     (2006.01)
*A61B 5/02*     (2006.01)
(Continued)

(52) U.S. Cl.
CPC ............ *A61B 5/7221* (2013.01); *A61B 5/002* (2013.01); *A61B 5/02* (2013.01); *A61B 5/022* (2013.01);
(Continued)

(58) Field of Classification Search
CPC ......... A61B 5/7221; A61B 5/02; A61B 5/022; A61B 5/002; A61B 5/02108;
(Continued)

(56) References Cited

U.S. PATENT DOCUMENTS

2001/0003792 A1* 6/2001 Ogura ................ A61B 5/02125
                                                          600/500
2017/0323069 A1* 11/2017 Bates .................... A61B 5/7221

FOREIGN PATENT DOCUMENTS

JP          62-34531        2/1987
JP          2004-113811     4/2004
(Continued)

OTHER PUBLICATIONS

International Search Report dated Oct. 24, 2017 in International (PCT) Application No. PCT/JP2017/031862.

*Primary Examiner* — Devin B Henson
*Assistant Examiner* — Justin Xu
(74) *Attorney, Agent, or Firm* — Wenderoth, Lind & Ponack, L.L.P.

(57) ABSTRACT

A blood pressure measurement apparatus includes a measuring device that includes a plurality of pressure sensors and is for measuring blood pressure information for each heartbeat in a measurement target, and an arrangement state inferring unit for extracting a feature quantity from an output waveform of each of the pressure sensors for each heartbeat, and inferring an arrangement state of the measuring means relative to an artery that is the measurement target based on a distribution profile of values of the feature quantity for the plurality of pressure sensors. The apparatus also includes a reliability calculating unit for calculating a reliability of the blood pressure information measured by the measuring means, based on the inferred arrangement state.

13 Claims, 23 Drawing Sheets

(51) Int. Cl.
A61B 5/021 (2006.01)
A61B 5/022 (2006.01)

(52) U.S. Cl.
CPC ...... A61B 5/02108 (2013.01); A61B 5/02233 (2013.01); A61B 5/6824 (2013.01); A61B 5/743 (2013.01); A61B 5/7405 (2013.01)

(58) Field of Classification Search
CPC . A61B 5/02233; A61B 5/6824; A61B 5/7405; A61B 5/743
See application file for complete search history.

(56) References Cited

FOREIGN PATENT DOCUMENTS

| | | |
|---|---|---|
| JP | 2004-222847 | 8/2004 |
| JP | 2012-223267 | 11/2012 |
| JP | 2014-195500 | 10/2014 |
| WO | WO2013068955 A1 * | 5/2013 |

* cited by examiner

BLOOD PRESSURE MEASUREMENT APPARATUS, METHOD OF CONTROLLING BLOOD PRESSURE MEASUREMENT APPARATUS, AND PROGRAM

TECHNICAL FIELD

The present invention relates to an apparatus for blood pressure measurement and a method of controlling the same, and more specifically relates to an apparatus for performing blood pressure measurement by tonometry.

BACKGROUND ART

A tonometry type of blood pressure measurement method is known in which an artery near the body surface, such as a radial artery, is pressed to the extent that a flattened portion is formed in the artery, the artery internal pressure and the external pressure are balanced, and the blood pressure is measured non-invasively by a pressure sensor. According to this method, it is possible to non-invasively obtain a blood pressure value for each heartbeat.

When blood pressure measurement is performed by tonometry, the pressure sensor needs to be accurately placed above an artery. In view of this, real apparatuses are provided with multiple micro pressure sensors, the most suitable output is selected as the blood pressure waveform from among the output of the group of sensors, and the blood pressure value is measured based on the selected output. For example, Patent Literature 1 discloses a method for selecting the most suitable output.

CITATION LIST

Patent Literature

Patent Literature 1: JP 2004-222847A

SUMMARY OF INVENTION

Technical Problem

Patent Literature 1 describes the following most suitable output selection method. Specifically, a sensor array has a pressing surface on which multiple pressure sensors are mounted, the sensor array is pressed against the body surface, and multiple voltage signals indicating pressure information are received at the same time from the pressure sensors when performing pulse wave detection. A CPU extracts, from each of the voltage signals, a direct current component that indicates a pressure component generated due to a solid object, and specifies the pressure sensors that are located above a solid object based on the extracted direct current components. The pressure sensors other than the specified pressure sensors located above a solid object are then selected as candidates for pressure sensors that are located above an artery, and a pulse wave generated from an artery is detected based on the pressure information output by the selected pressure sensors.

According to this type of technique, in cases where the measurement value is significantly affected by pressure sensors that are arranged on solid objects other than an artery, it is possible to specify sensors that are in an unsuitable arrangement, and exclude such sensors from the candidates for selection of a most suitable output value.

However, with the above-described conventional technique, there is a problem that even if output is acquired under conditions that negatively influence data analysis, such as the case of shift in the direction in which the artery is pressed (the sensor group is arranged tilted relative to the pressed surface), such a case is treated the same as the case where the sensor group is arranged suitably.

In view of the above-described circumstances, an object of the present invention is to provide a technique for calculating the reliability of blood pressure information that is measured in a tonometry type of blood pressure measurement method.

Solution to Problem

In order to achieve the aforementioned object, the present invention employs configurations such as the following.

A blood pressure measurement apparatus according to the present invention is a blood pressure measurement apparatus that measures a blood pressure by tonometry, the blood pressure measurement apparatus including: a measuring means that includes a plurality of pressure sensors and is for measuring blood pressure information for each heartbeat in a measurement target; an arrangement state inferring means for extracting a feature quantity from an output waveform of each of the pressure sensors for each heartbeat, and inferring an arrangement state of the measuring means relative to an artery that is the measurement target based on a distribution profile of values of the feature quantity for the plurality of pressure sensors; and a reliability calculating means for calculating a reliability of the blood pressure information measured by the measuring means, based on the inferred arrangement state.

According to this configuration, it is possible to obtain a reliability regarding the measured blood pressure information, and blood pressure information obtained when the measuring means is in an unsuitable arrangement state (i.e., a measurement value having a low reliability) can be prevented from being treated similarly to blood pressure information obtained when the measuring means is in a suitable arrangement state (i.e., a measurement value having a high reliability).

Here, the arrangement state inferring means may extract, from the output waveform of each of the pressure sensors for each heartbeat, a difference value between a maximum value and a minimum value in the output waveform, and/or the minimum value, as the feature quantity, and estimate the arrangement state of the measuring means based on a distribution profile of the difference value for the plurality of pressure sensors and/or a distribution profile of the minimum value.

Also, the measuring means may have at least one sensor array that is constituted by a plurality of pressure sensors that are arranged side-by-side in a direction that intersects the artery during measurement.

According to this configuration having a group of pressure sensors in a predetermined arrangement, the distribution profile of the feature quantity can be understood to include the predetermined arrangement, and the arrangement state can be inferred efficiently.

Also, the arrangement state may include a pressing extent that indicates an extent of force that the sensor array applies to the artery, and the arrangement state inferring means may infer the pressing extent based on a difference between a peak value and a bottom value in the distribution profile of the difference value and/or the peak value in the distribution profile of the difference value.

According to this configuration in which the arrangement state includes the pressing extent, in the case where blood pressure information is measured in a state where the extent of the force applied by the sensor array to the artery is unsuitable, it is possible to obtain a reliability of the blood pressure information that reflects this state.

Furthermore, the arrangement state may include a width direction tilt that indicates tilt in a direction perpendicular to a direction of extension of the artery, relative to a reference state that is an orientation suited to measurement, and the arrangement state inferring means may infer the width direction tilt based on an inclination in the distribution profile of the minimum value.

According to this configuration in which the arrangement state includes the width direction tilt, in the case where blood pressure information is measured in a state where the measuring means is tilted in a direction perpendicular to the extending direction of the artery relative to the suitable state, it is possible to obtain a reliability of the blood pressure information that reflects this state.

Moreover, the arrangement state may include a width direction shift that indicates shift in a direction perpendicular to a direction of extension of the artery, relative to a reference state that is an orientation suited to measurement, and the arrangement state inferring means may infer the width direction shift based on a position of a peak in the distribution profile of the difference value.

According to this configuration in which the arrangement state includes the width direction shift, in the case where blood pressure information is measured in a state where the measuring means is shifted in a direction perpendicular to the extending direction of the artery relative to the suitable state, it is possible to obtain a reliability of the blood pressure information that reflects this state.

Moreover, the measuring means may include a first sensor array and a second sensor array that are arranged parallel with each other, the arrangement state may include an artery direction tilt that indicates tilt in a direction parallel to a direction of extension of the artery, relative to a reference state that is an orientation suited to measurement, and the arrangement state inferring means may infer the artery direction tilt based on a difference between a peak value and a bottom value in the distribution profile of the difference value and the peak value in the distribution profile of the difference value for each of the first sensor array and the second sensor array.

In this way, due to the fact that the sensor group having a predetermined arrangement is provided in two rows arranged parallel to each other, it is possible to efficiently estimate a wider variety of arrangement states of the measuring means. Also, due to the fact that the arrangement state includes the artery direction tilt of the measuring means, in the case where blood pressure information is measured in a state where the measuring means is tilted in a direction parallel to the extending direction of the artery relative to the suitable state, it is possible to obtain a reliability of the blood pressure information that reflects this state.

Moreover, the measuring means may include a first sensor array and a second sensor array that are arranged parallel with each other, the arrangement state may include an artery direction shift that indicates shift in a direction parallel to a direction of extension of the artery, relative to a reference state that is an orientation suited to measurement, and the arrangement state inferring means may infer the artery direction shift based on a difference between peak values in the distribution profiles of the difference values of the first sensor array and the second sensor array.

According to this configuration in which the arrangement state includes the artery direction shift, in the case where blood pressure information is measured in a state where the measuring means is shifted in a direction parallel to the extending direction of the artery relative to the suitable state, it is possible to obtain a reliability of the blood pressure information that reflects this state.

Moreover, the measuring means may include a first sensor array and a second sensor array that are arranged parallel with each other, the arrangement state may include a rotation shift that indicates rotation of the sensor array in a plane of contact with the measurement target, relative to a reference state that is an orientation suited to measurement, and the arrangement state inferring means may infer the rotation shift based on a difference between positions of peaks in the distribution profiles of the difference values of the first sensor array and the second sensor array.

According to this configuration in which the arrangement state includes the rotation direction shift, in the case where blood pressure information is measured in a state where the sensor array is shifted in the rotation direction in the plane of contact with the measurement target, it is possible to obtain a reliability of the blood pressure information that reflects this state.

Also, the blood pressure measurement apparatus according to the present invention may further include an outputting means for outputting one of or a combination of the blood pressure information, the arrangement state, and the reliability.

According to this configuration having the outputting means, the various types of information can be appropriately output for use.

Moreover, the outputting means may be one of or a combination of an image displaying means for outputting one of or a combination of the blood pressure information, the arrangement state, and the reliability, using text and/or an image, a sound outputting means for outputting one of or a combination of the blood pressure information, the arrangement state, and the reliability, using a sound, and a communicating means for outputting, to another apparatus, one of or a combination of the blood pressure information, the arrangement state, and the reliability, using wired or wireless communication.

According to this configuration, it is possible to employ a suitable output method according to the information that is to be output and the objective, and by having multiple different outputting means, it is possible to more effectively output information.

Also, the blood pressure measurement apparatus according to the present invention may further include a warning means for outputting, to the outputting means, information indicating an unsuitable arrangement state that causes a decrease in the reliability, in a case where the reliability is less than or equal to a predetermined reference value.

According to this configuration, in the case where the reliability of the blood pressure information is less than or equal to a predetermined reference value, the user of the blood pressure measurement apparatus can find out that fact and the cause for it.

Moreover, the blood pressure measurement apparatus according to the present invention may further include a correction instructing means for outputting, to the outputting means, a method of correcting an unsuitable arrangement state that causes a decrease in the reliability to a suitable arrangement state, in a case where the reliability is less than or equal to a predetermined reference value.

According to this configuration, in the case where the reliability of the blood pressure information is less than or equal to the predetermined reference value, the user of the blood pressure measurement apparatus can, in accordance with the correction instruction, correct the measuring means to a suitable arrangement state.

Also, the blood pressure measurement apparatus according to the present invention may be a wearable apparatus for being attached to a wrist.

According to this configuration, the user of the blood pressure measurement apparatus can measure their blood pressure without the freedom of body movement being constrained.

A method of controlling a blood pressure measurement apparatus according to the present invention includes: a measuring step of, with use of a measuring means that includes a plurality of pressure sensors, measuring blood pressure information for each heartbeat in a measurement target; a step of extracting a feature quantity from an output waveform of each of the pressure sensors for each heartbeat; a step of inferring an arrangement state of the measuring means relative to an artery that is the measurement target based on a distribution profile of values of the feature quantity for the plurality of pressure sensors; and a step of calculating a reliability of the blood pressure information measured by the measuring means, based on the inferred arrangement state.

A program according to the present invention causes the steps of the above-described method of controlling a blood pressure measurement apparatus to be executed by the blood pressure measurement apparatus.

Note that the present invention can be understood as a blood pressure measurement apparatus that has at least some of the configurations and functions described above. Also, the present invention can be understood as a method of controlling a blood pressure measurement apparatus that includes at least some of the above processing steps, a program for causing a computer (processor) to execute this method, or a computer-readable recording medium on which this program is non-transitorily recorded. The present invention can be configured by combining the above-described configurations and processing steps as long as no technical contradiction arises.

Advantageous Effects of Invention

According to the present invention, it is possible to provide a technique for calculating the reliability of blood pressure information that is measured in a tonometry type of blood pressure measurement method.

DESCRIPTION OF EMBODIMENTS

Hereinafter, specific embodiments of the present invention will be described with reference to the drawings. Unless otherwise stated in particular, the dimensions, materials, shapes, relative arrangements, and the like of constituent elements described in the following embodiments are not intended to limit the technical scope of this invention.

First Embodiment

First, a first embodiment of the present invention will be described with reference to FIGS. 1 to 19. A blood pressure measurement apparatus according to the present embodiment is an apparatus for measuring the pressure pulse wave of a radial artery by tonometry. Here, tonometry refers to a method in which an artery is pressed from above the skin with suitable pressure so as to form a flattened portion in the artery, the artery internal pressure and the external pressure are balanced, and a pressure pulse wave is measured non-invasively by pressure sensors.

Configuration of Blood Pressure Measurement Apparatus

Figure 1:
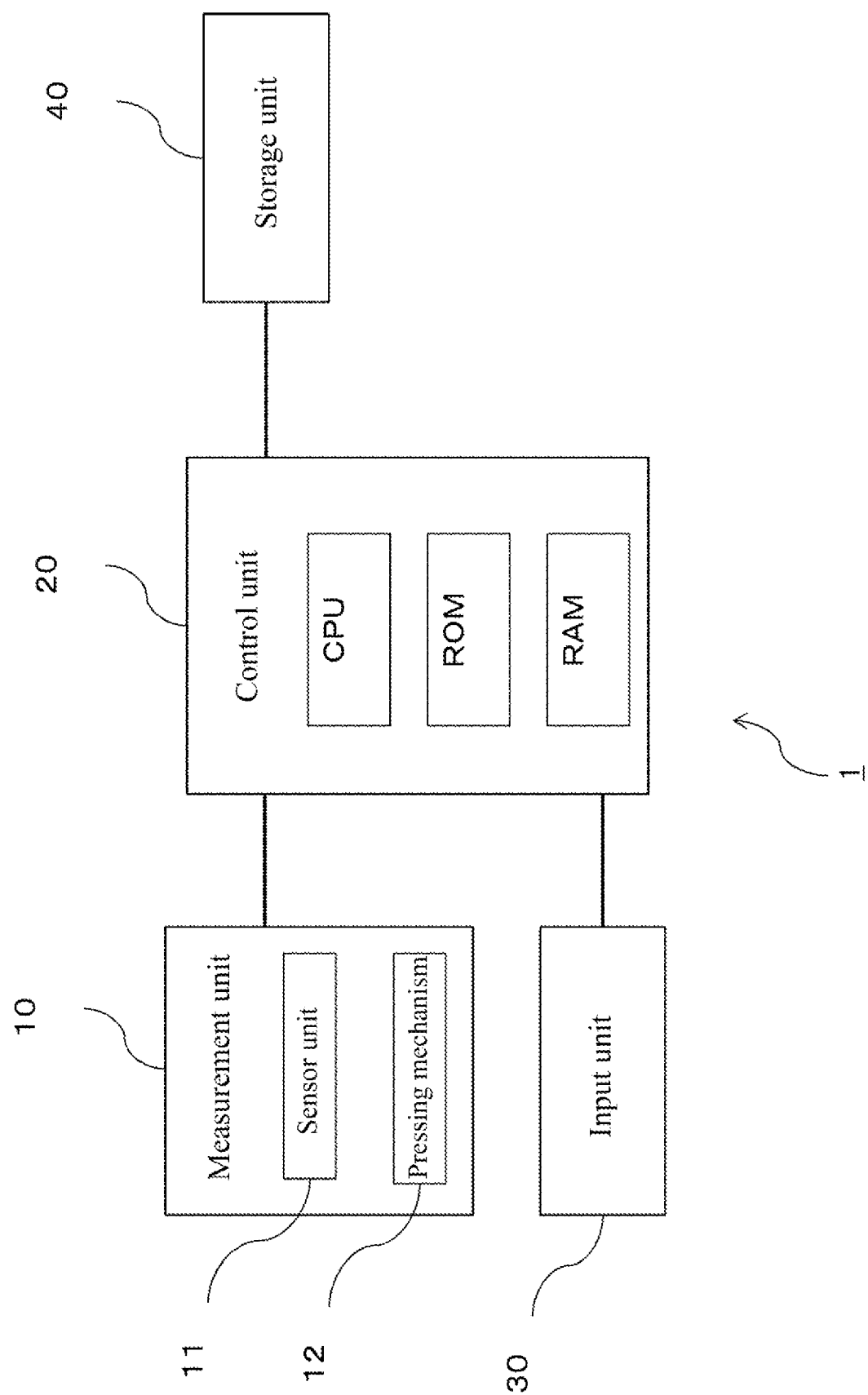
FIG. 1 is a block diagram showing an overall configuration of a blood pressure measurement apparatus according to a first embodiment of the present invention.

FIG. 1 is a block diagram showing the overall configuration of a blood pressure measurement apparatus 1 according to the present embodiment. The blood pressure measurement apparatus 1 mainly has a measurement unit 10, a control unit 20, an input unit 30, and a storage unit 40.

Note that the blood pressure measurement apparatus 1 may be a stationary type of apparatus that is used in the state where the upper arm of a measurement subject is placed on a fixing base during measurement, or may be a wearable apparatus that is attached in a manner of not restricting movement of the measurement subject during measurement. Here, in the case where the blood pressure measurement apparatus 1 is a wearable apparatus, movement of the measurement subject is not restricted, but the blood pressure measurement apparatus 1 tends to deviate from a state that is suitable for blood pressure measurement. In view of this, with the apparatus of the present embodiment that can obtain the degree of reliability of measured blood pressure information, it is possible to prevent blood pressure information that was measured in an unsuitable state from being treated the same as blood pressure information that was measured in a suitable state, and therefore such an apparatus is preferable.

Figure 2:
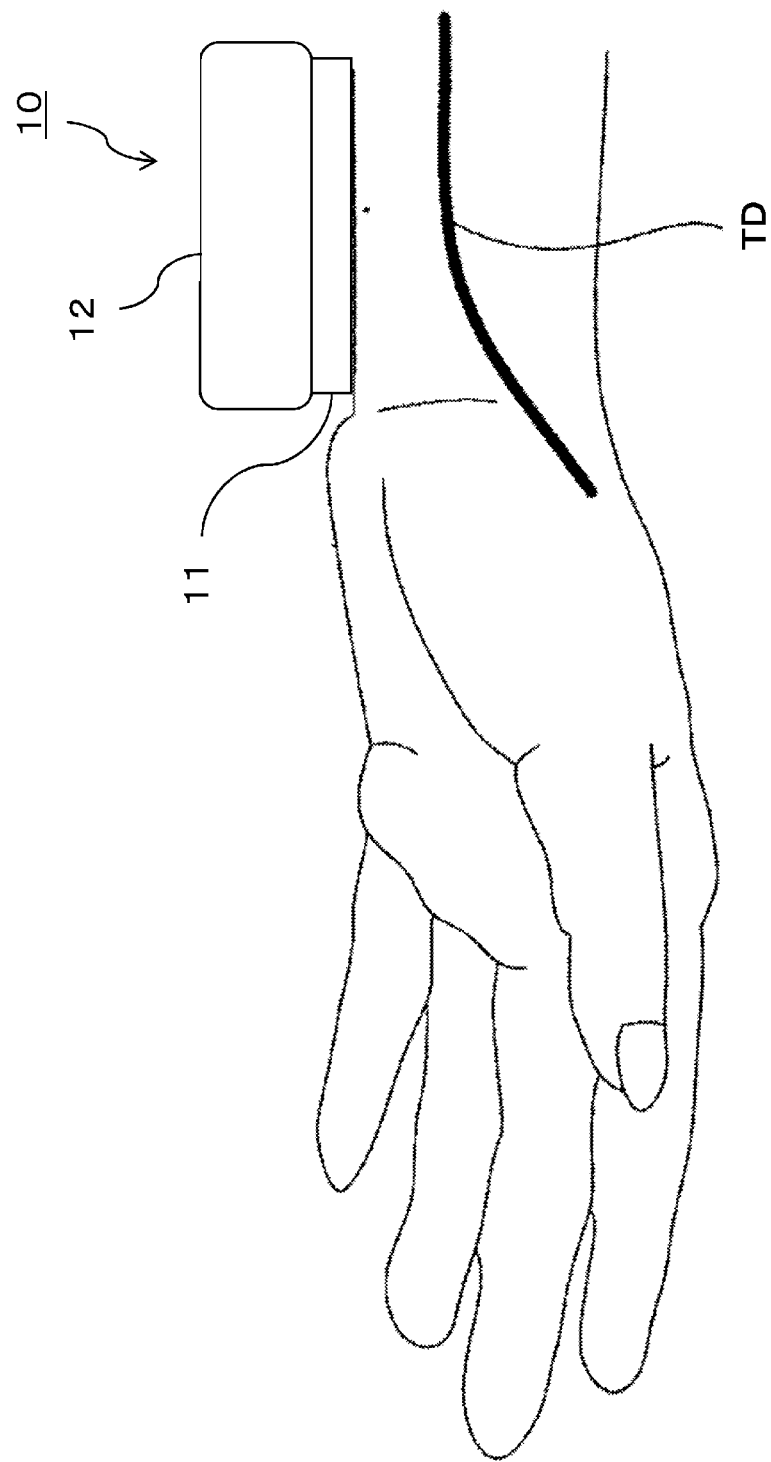
FIG. 2 is a diagram showing a state where a measurement unit of the blood pressure measurement apparatus of the first embodiment is attached to the left wrist of a measurement subject by a belt that is not shown.
Figure 3:
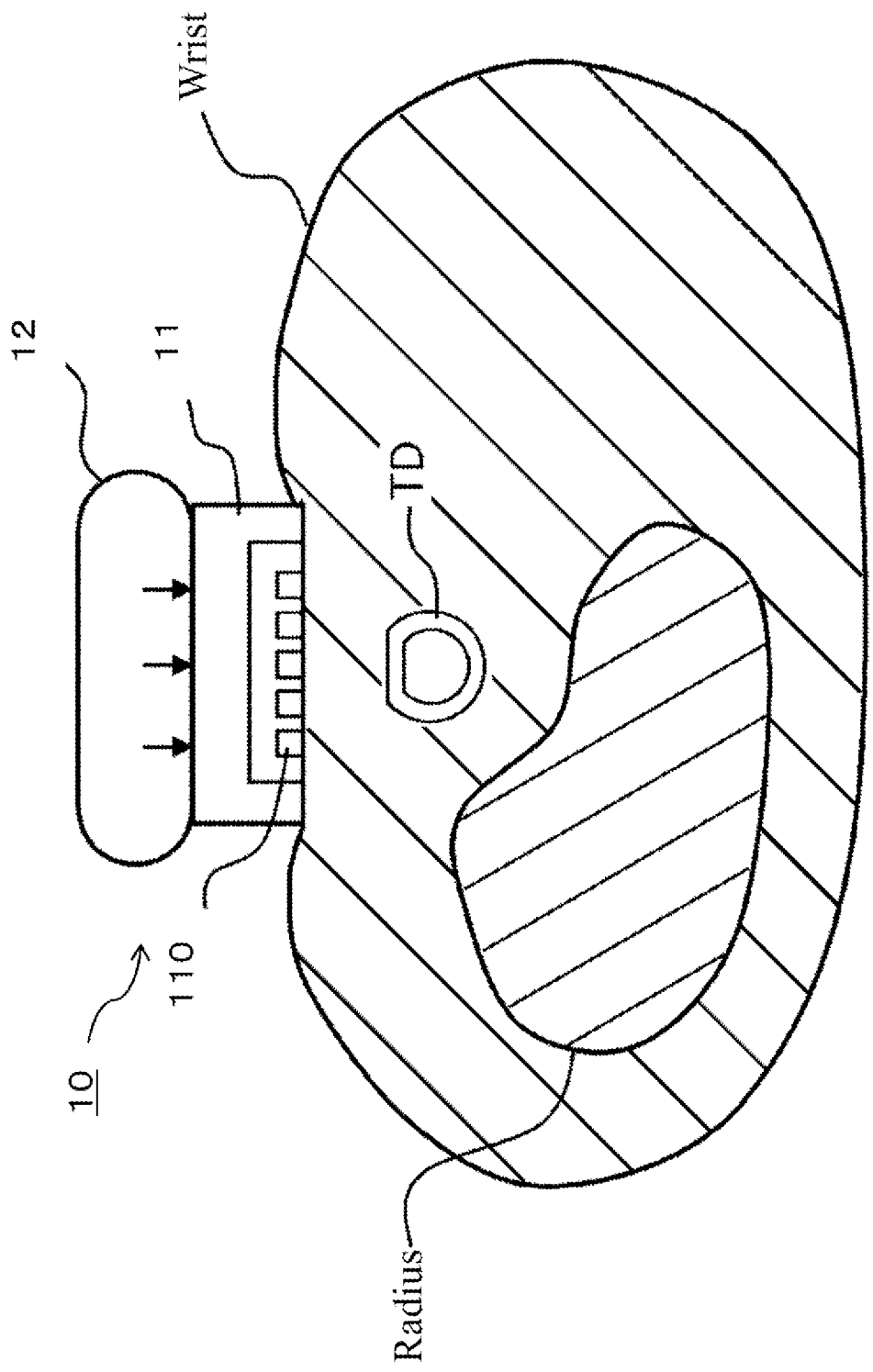
FIG. 3 is a cross-sectional diagram schematically showing the structure of the measurement unit of the blood pressure measurement apparatus of the first embodiment, and the state thereof during measurement.

The measurement unit 10 measures the pressure pulse wave of a measurement subject with use of a sensor unit 11. FIG. 2 is a diagram showing a state where the measurement unit 10 is attached to the left wrist of the measurement subject by a belt that is not shown, and FIG. 3 is a cross-sectional diagram schematically showing the structure of the measurement unit 10 and the state thereof during measurement. As shown in FIGS. 2 and 3, the measurement unit 10 includes a sensor unit 11 and a pressing mechanism 12 for pressing the sensor unit 11 against the wrist, and the measurement unit 10 is arranged so as to come into contact with the body surface at the location of a radial artery TD that is the blood pressure measurement target.

Figure 4:
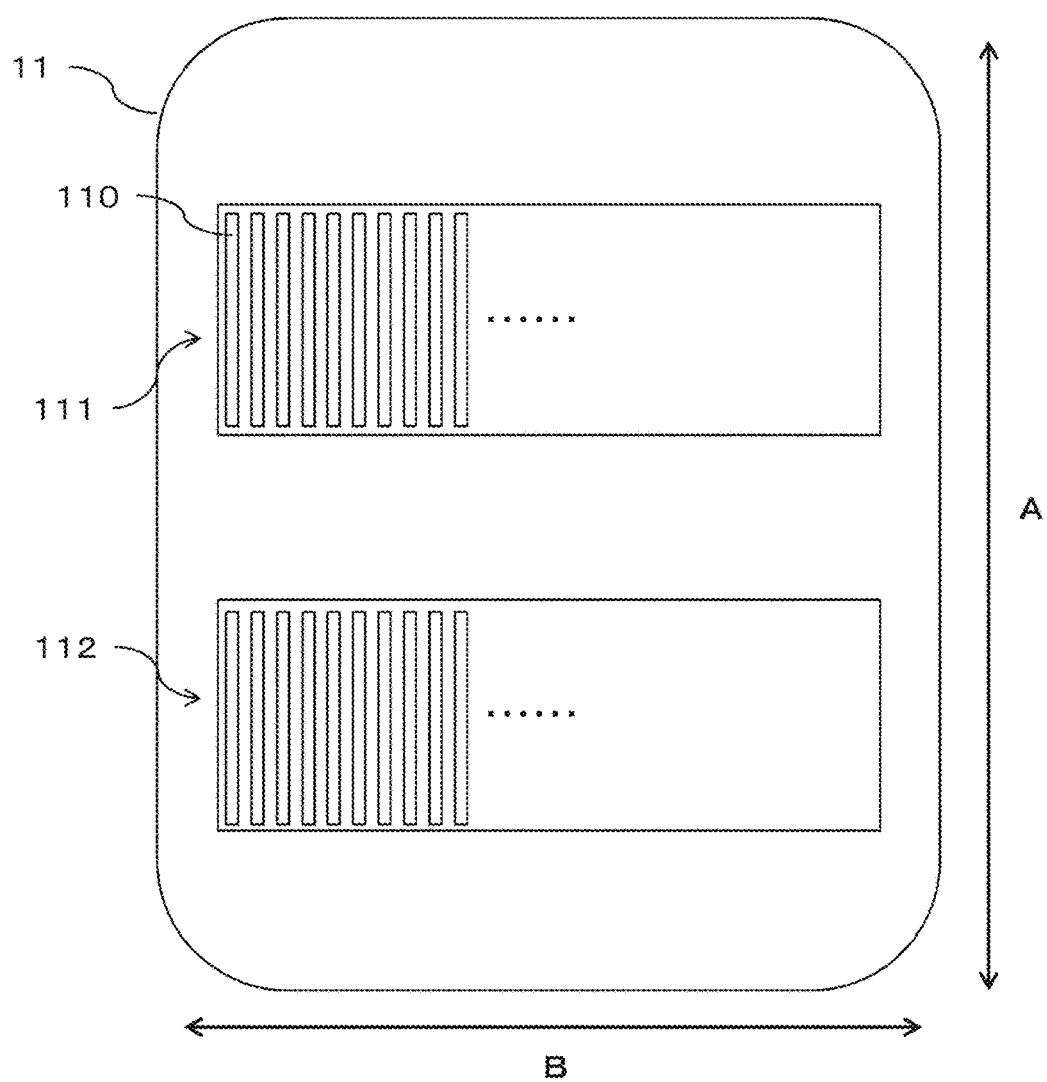
FIG. 4 is a diagram showing a side surface of a sensor unit that comes into contact with a body surface in the blood pressure measurement apparatus of the first embodiment.

FIG. 4 is a diagram showing a side surface of a sensor unit 11 that comes into contact with the body surface. As shown in FIG. 4, the sensor unit 11 has a first sensor array 111 that is formed by multiple (e.g., 46) pressure sensors 110 that are arranged side-by-side in a direction B that intersects a direction A, which is the direction of extension of the radial artery TD that is located at the attachment site when the measurement unit 10 is attached, and a second sensor array 112 that is arranged parallel with the first sensor array 111.

The pressure sensors 110 that constitute the first and second sensor arrays 111 and 112 are arranged with intervals therebetween according to which a necessary and sufficient number of pressure sensors are arranged above the radial artery TD, and furthermore the pressure sensors 110 in each of the sensor arrays are arranged so as to form pairs with the pressure sensors 110 that constitute the other sensor array. Here, a piezoelectric element that measures pressure and converts it into an electrical signal, an element that employs the piezoresistance effect, or the like can be preferably used as the pressure sensors 110.

The pressing mechanism 12 is constituted by an air bag and a pump that adjusts the internal pressure of the air bag, for example. When the control unit 20 controls the pump so as to raise the internal pressure of the air bag, the pressure sensors 110 are pressed against the body surface by expansion of the air bag. Note that the pressing mechanism 12 may be any mechanism that is capable of adjusting the force for pressing the pressure sensors 110 against the body surface, and is not limited to being a mechanism that uses an air bag.

The control unit 20 performs various types of processing, such as controlling units of the blood pressure measurement apparatus 1, recording and analyzing measured data, and inputting and outputting data. The control unit 20 includes a processor, a ROM (Read Only Memory), a RAM (Random Access Memory), and the like. The later-described functions of the control unit 20 are realized by the processor reading out programs stored in the ROM or the storage unit 40 and executing the programs. The RAM functions as a work memory when the control unit 20 performs various types of processing.

The input unit 30 provides an operation interface to the user. For example, it is possible to use operation buttons, switches, a touch panel, or the like.

The storage unit 40 is a storage medium that enables the storage and reading of data, and stores programs executed by the control unit 20, measurement data obtained from the measurement unit 10, various types of data obtained by processing the measurement data, and the like. A flash memory, for example, is used as the storage unit 40. The storage unit 40 may be a portable memory such as a memory card, or may be built into the blood pressure measurement apparatus 1.

Functions of Control Unit

Figure 5:
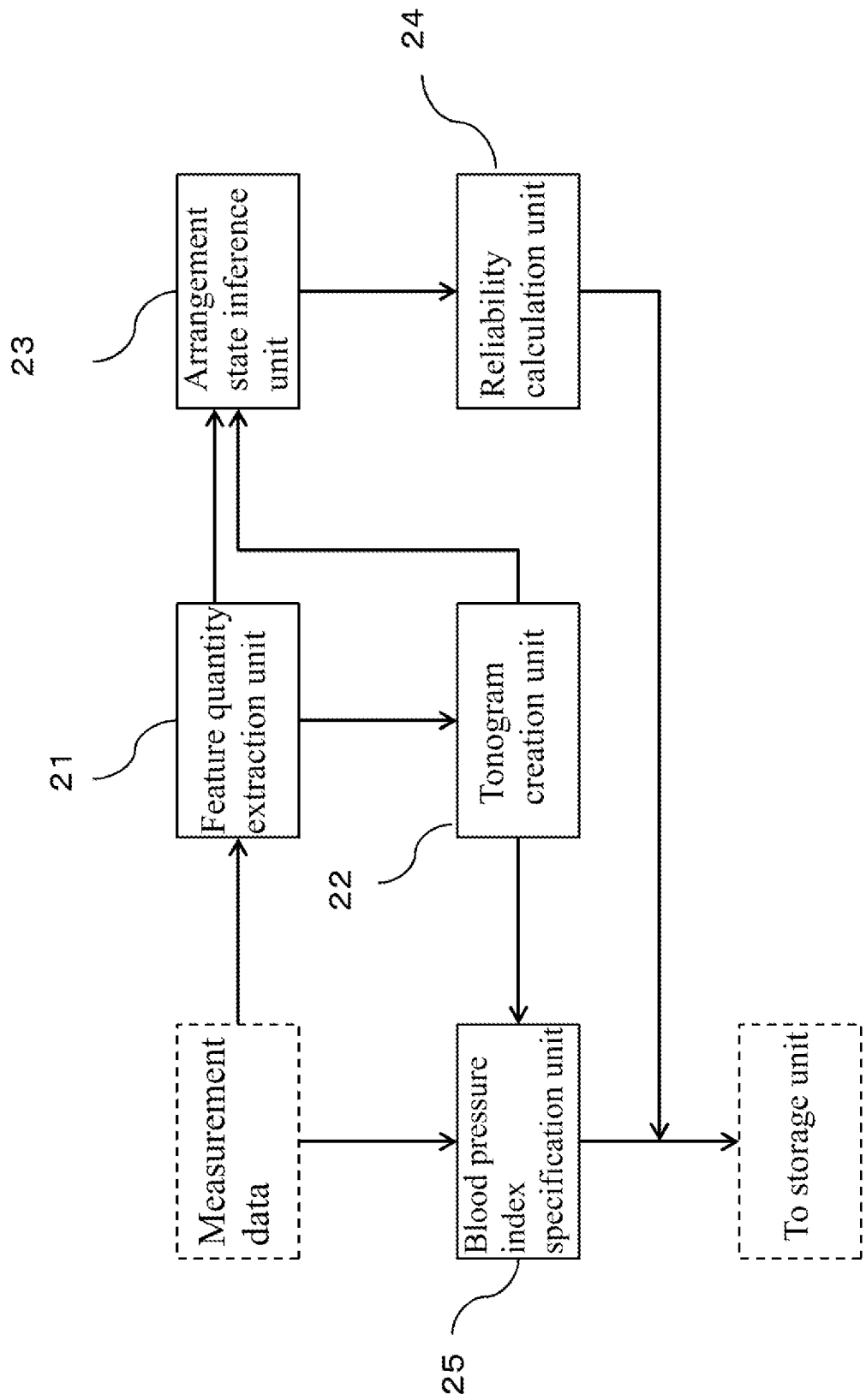
FIG. 5 is a block diagram showing an overview of a functional configuration of a control unit of the blood pressure measurement apparatus of the first embodiment.

FIG. 5 is a block diagram showing an overview of the functional configuration of the control unit 20. As shown in FIG. 5, as basic functions, the control unit 20 has a feature quantity extraction unit 21, a tonogram creation unit 22, an arrangement state inference unit 23, a reliability calculation unit 24, and a blood pressure index specification unit 25. In the present embodiment, the functions of these units are realized by the control unit 20 executing necessary programs.

The feature quantity extraction unit 21 is a function for extracting feature quantities from an arterial pressure waveform measured by the blood pressure measurement unit for each heartbeat. The feature quantities that are extracted in the present embodiment are, for example, the maximum pressure value and the minimum pressure value of each heartbeat, and the difference value between the maximum pressure value and the minimum pressure value.

The tonogram creation unit 22 is a function for creating a tonogram. Here, the term "tonogram" refers to the distribution profile of the values of the feature quantity for the plurality of pressure sensors. In the present embodiment, a tonogram is created for each of the sensor arrays based on the difference value between the maximum pressure value and the minimum pressure value of each heartbeat (called the "ac component" hereinafter), and the minimum pressure value (called the "dc component" hereinafter), which are extracted by the feature quantity extraction unit 21.

The arrangement state inference unit 23 is a function for inferring the arrangement state of the sensor unit 11 relative to the radial artery TD, based on the shape of a tonogram. In the present embodiment, a final inference is made from among 64 patterns of arrangement states.

The reliability calculation unit 24 is a function for calculating a reliability of blood pressure information measured by the measurement unit 10, based on the inferred arrangement state of the sensor unit 11.

The blood pressure index specification unit 25 is a function for specifying blood pressure indices that are to be final measurement values, based on blood pressure information measured by multiple pressure sensors 110. The blood pressure indices that are specified in the present embodiment are the systolic blood pressure (SBP), the diastolic blood pressure (DBP), and the pulse rate (PR).

Functions of Blood Pressure Measurement Apparatus

Figure 6:
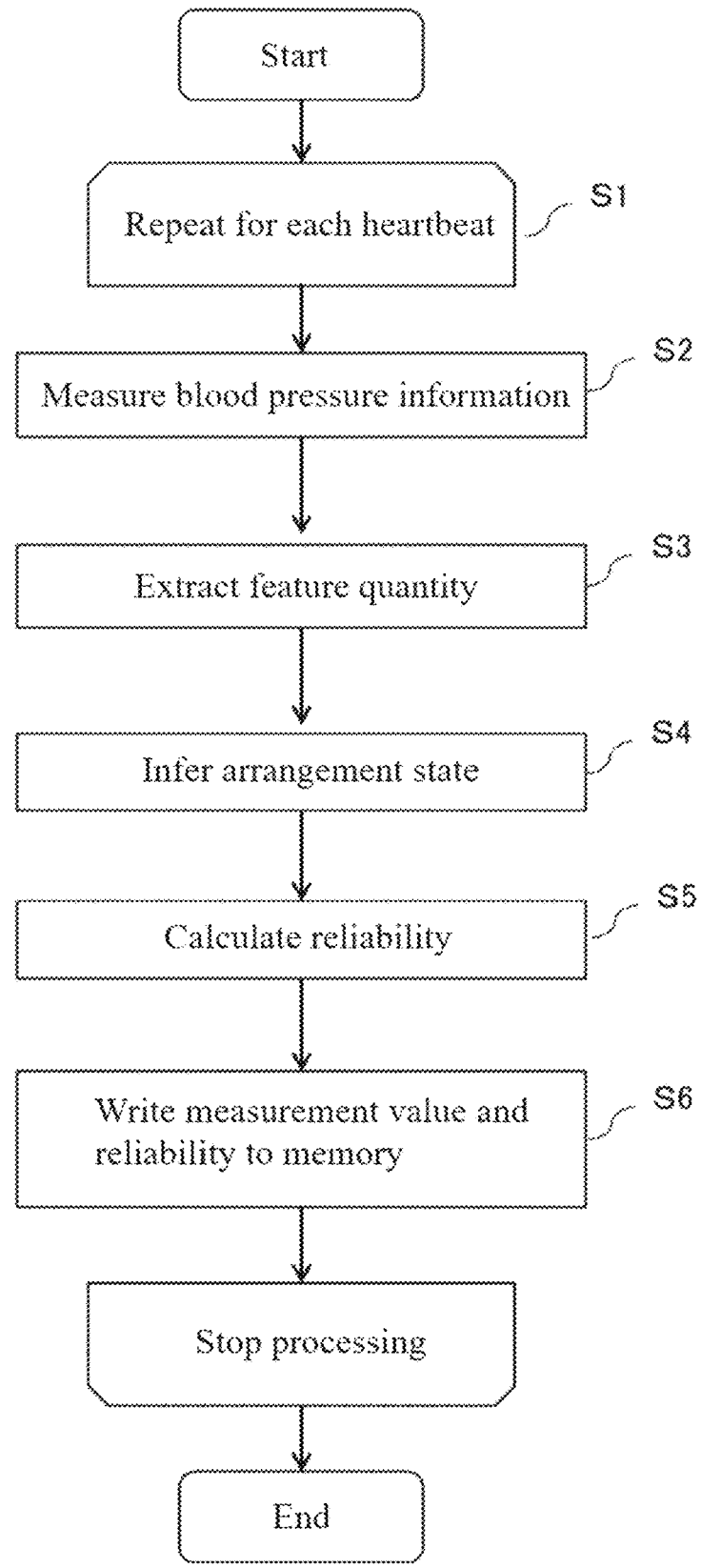
FIG. 6 is a flowchart showing an example of the overall flow of processing performed by the blood pressure measurement apparatus of the first embodiment.

The following describes functions of the blood pressure measurement apparatus 1 in the present embodiment. FIG. 6 is a flowchart showing an example of the overall flow of processing performed by the blood pressure measurement apparatus 1 of the present embodiment. As shown in FIG. 6, for each heartbeat, the blood pressure measurement apparatus 1 measures blood pressure information (step S2), extracts feature quantities from the measured information and creates a tonogram (step S3), infers the arrangement state of the sensor unit 11 relative to the radial artery TD based on the tonogram (step S4), calculates a reliability based on the inferred arrangement state (step S5), and records the reliability and the measured blood pressure information to the storage unit 40 (step S6).

Measurement of Blood Pressure Information

When the measurement unit 10 is attached to the wrist and the blood pressure measurement apparatus 1 is started up, the control unit 20 controls the pressing mechanism 12 of the measurement unit 10 and keeps the pressing force applied to the sensor unit 11 in a suitable state. The control unit 20 then successively receives blood pressure information measured by the pressure sensors 110.

Figure 7:
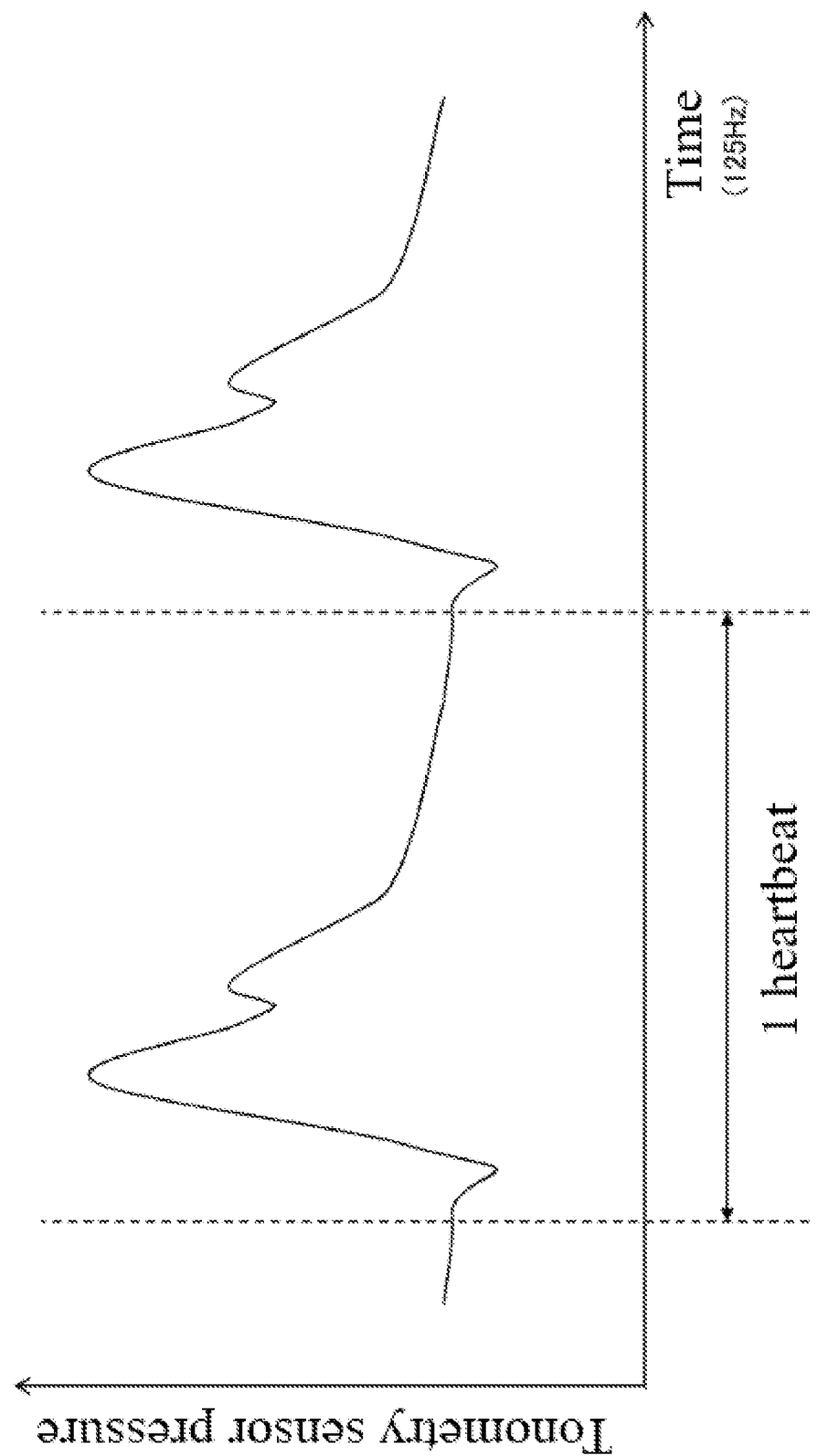
FIG. 7 is a diagram showing an arterial pressure waveform measured by the pressure sensor.

FIG. 7 shows an arterial pressure waveform (tonometry sensor pressure) measured by a pressure sensor 110. The horizontal axis indicates time, and the vertical axis indicates the blood pressure. The sampling frequency is 125 Hz in the present embodiment, but can be set as desired, as long as it is possible to reproduce the shape features of a waveform for one heartbeat.

Feature Quantity Extraction, and Tonogram

Figure 8:
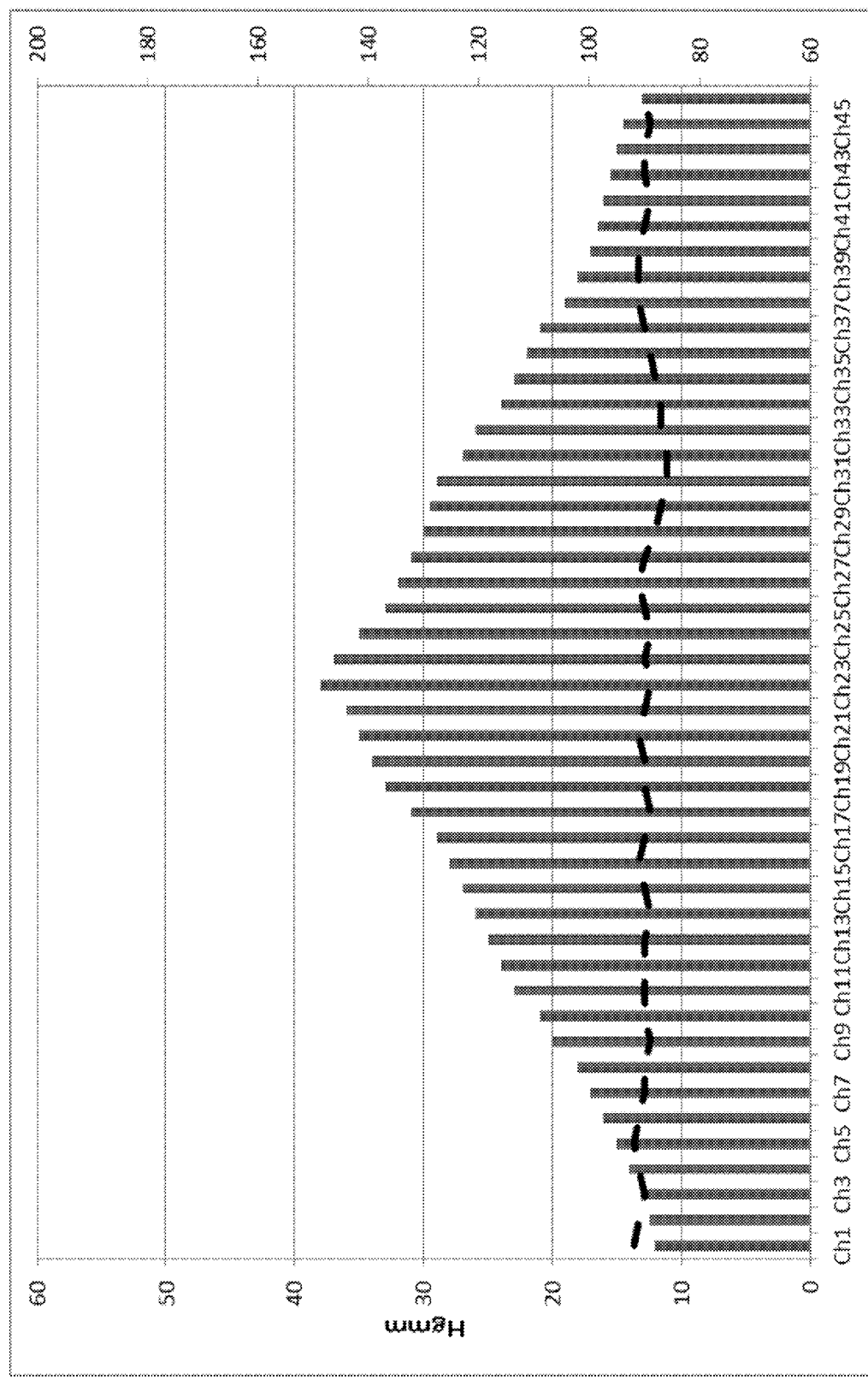
FIG. 8 is a diagram showing an example of a tonogram.

The feature quantity extraction unit 21 extracts an ac component and a dc component from the arterial pressure waveforms measured by the pressure sensors 110. Also, the tonogram creation unit 22 creates a graph, that is to say a tonogram, that plots, on the horizontal axis, the positions on a sensor array at which the pressure sensors 110 constituting it are located, and plots, on the vertical axis, the ac component and the dc component for each pressure sensor 110 in the same heartbeat. FIG. 8 is a diagram showing an example of the tonogram. The pressure sensors 110 are assigned channel numbers according to the positions at which they are arranged.

In the present embodiment, the pressure sensor 110 that has the highest ac component value (peak value) in each sensor array is considered to be the peak channel, and the pressure sensor 110 that has the lowest ac component value (bottom value) is considered to be the bottom channel. Also, the tonogram for the first sensor array 111 is called the first tonogram, and the peak value and the bottom value of the first tonogram are respectively called the first peak value and the first bottom value. Furthermore, the tonogram for the second sensor array 112 is called the second tonogram, and the peak value and the bottom value of the second tonogram are respectively called the second peak value and the second bottom value.

The blood pressure index specification unit 25 selects, as the active channel, whichever one of the peak channel of the first sensor array 111 and the peak channel of the second sensor array 112 has the larger ac component value, and specifies various blood pressure indices from the blood pressure information measured on the active channel.

Relationship Between Tonogram and Sensor Unit Arrangement State

Figure 9:
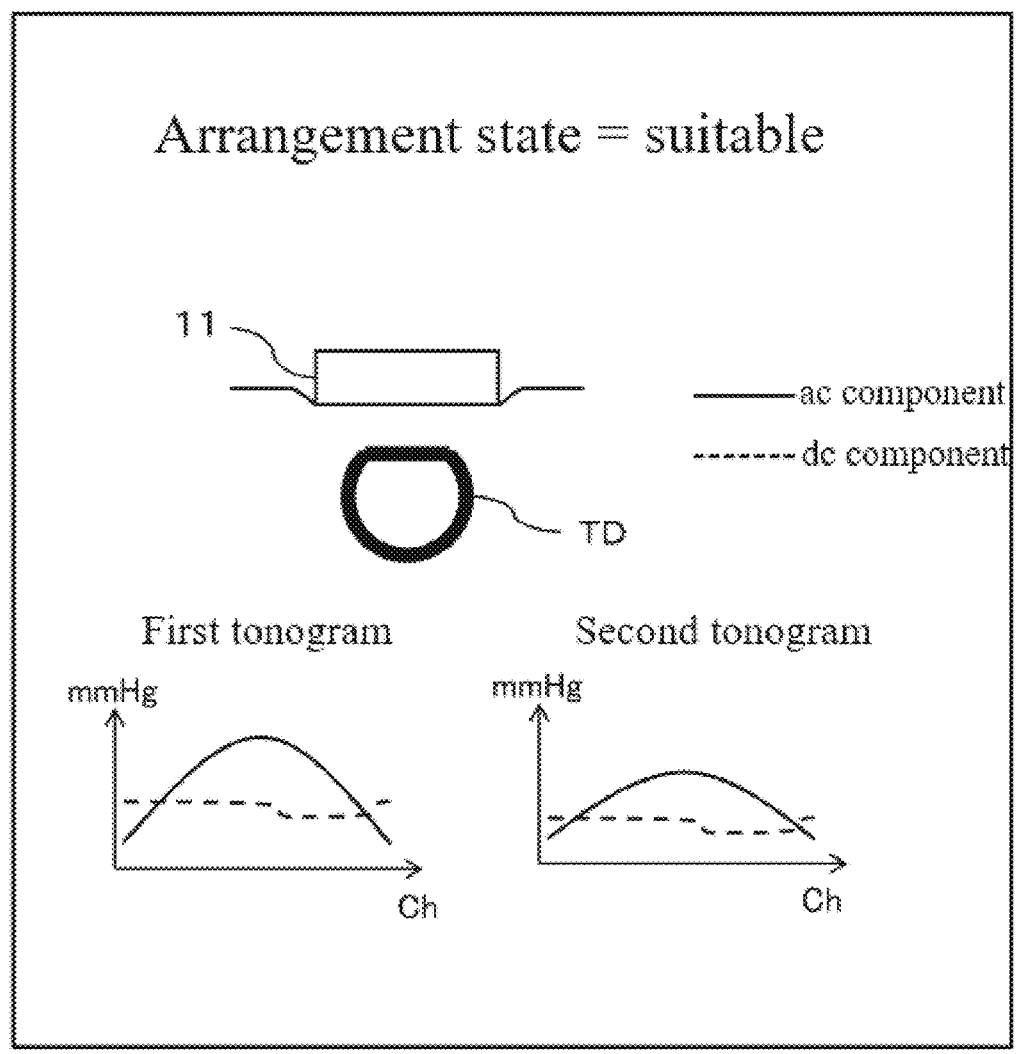
FIG. 9 is a diagram showing a state where the sensor unit of the blood pressure measurement apparatus of the first embodiment is suitably arranged relative to a radial artery, and the shapes of tonograms in this arrangement state.

FIG. 9 is a diagram showing a state where the sensor unit 11 is suitably arranged relative to the radial artery TD, and the shapes of tonograms in this arrangement state, and FIGS. 10, 11, 12, 13, 14, 15, and 16 are diagrams showing seven patterns in which the sensor unit 11 is not arranged suitably relative to the radial artery TD, and the shapes of tonograms in those arrangement states. Note that in the present specification, it is assumed that a suitable arrangement state is a state in which, out of the two sensor arrays, the first sensor array 111 is arranged at a location that is most suited to pulse pressure wave measurement.

As shown in FIG. 9, the state where the sensor unit 11 is arranged suitably relative to the radial artery TD is defined as the state in the case where the ac component of the first tonogram is shaped as mountain with the peak channel located at the approximate center, furthermore the ac component of the second tonogram is shaped as a somewhat flatter mountain than in the tonogram of the first sensor array 111, and furthermore the dc components of the first sensor array 111 and the second sensor array 112 have an approximately flat shape.

Figure 10:
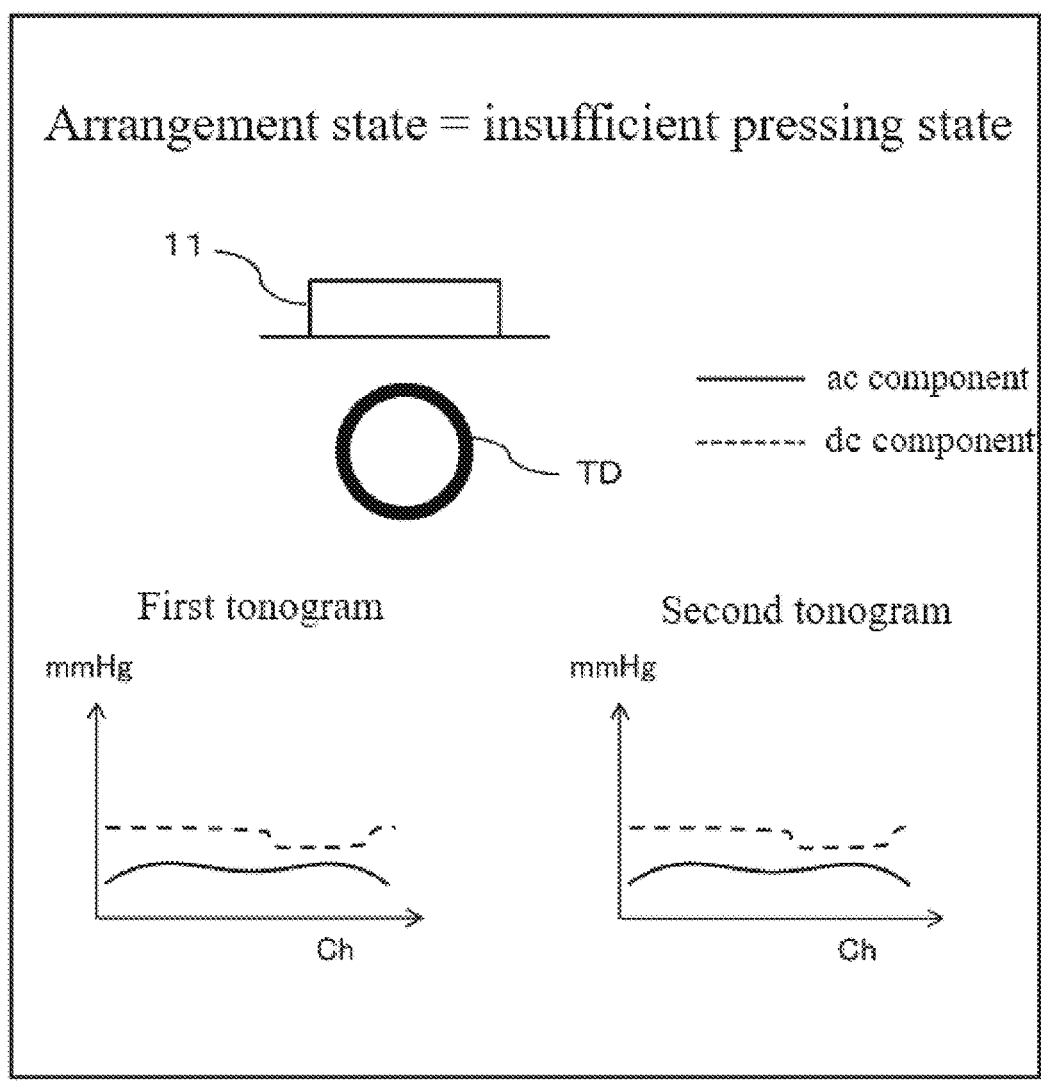
FIG. 10 is a diagram showing an arrangement state in which the sensor unit of the blood pressure measurement apparatus of the first embodiment is pressed insufficiently, and the shapes of tonograms in this arrangement state.

Accordingly, as shown in FIG. 10, in the case where in both the first tonogram and the second tonogram, the ac component and the dc component both have a flat shape with a low level (the peak value is low, and the difference between the peak value and the bottom value is small), it can be inferred that the arrangement state is a state in which the force for pressing the sensor unit 11 against the radial artery TD is too weak, that is to say an insufficient pressing state.

Figure 11:
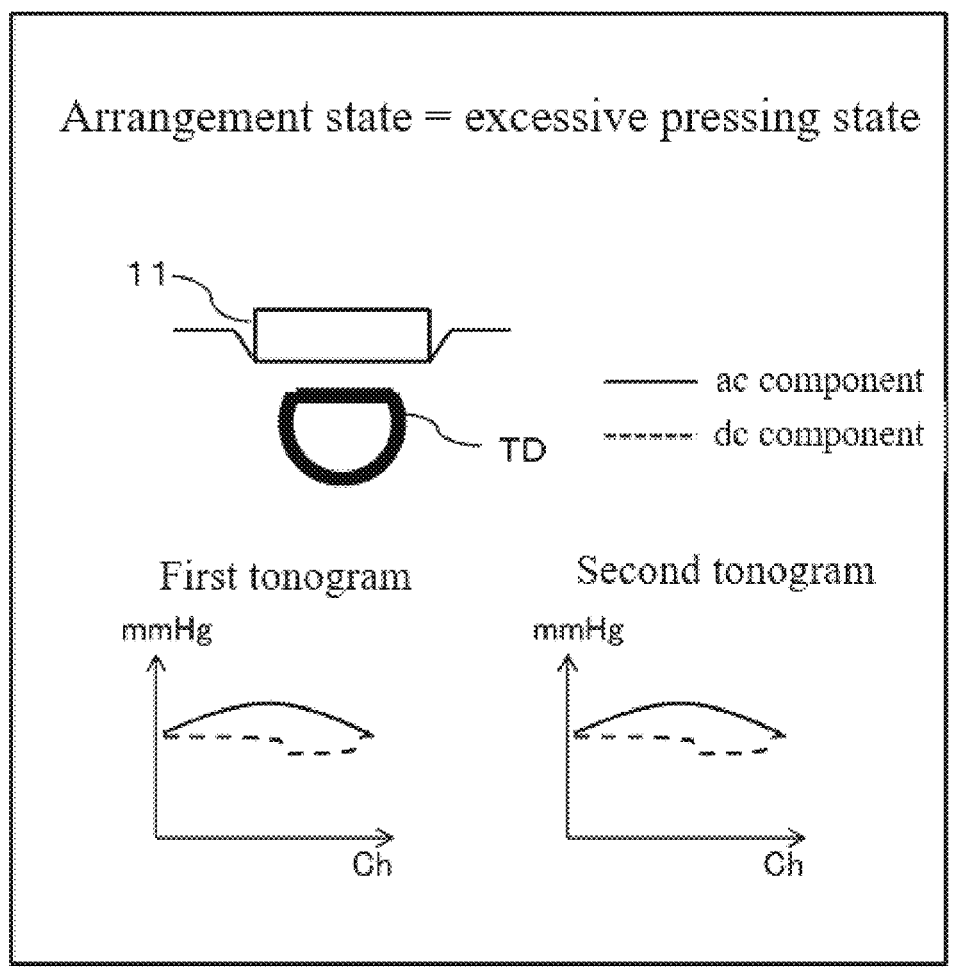
FIG. 11 is a diagram showing an arrangement state in which the sensor unit of the blood pressure measurement apparatus of the first embodiment is pressed excessively, and the shapes of tonograms in this arrangement state.

Also, as shown in FIG. 11, in the case where in both the first tonogram and the second tonogram, the ac component and the dc component both have a flat shape with a high level (the peak value is high, and the difference between the peak value and the bottom value is small), it can be inferred that the arrangement state is a state in which the force for pressing the sensor unit 11 against the radial artery TD is excessive, that is to say an excessive pressing state.

Figure 12:
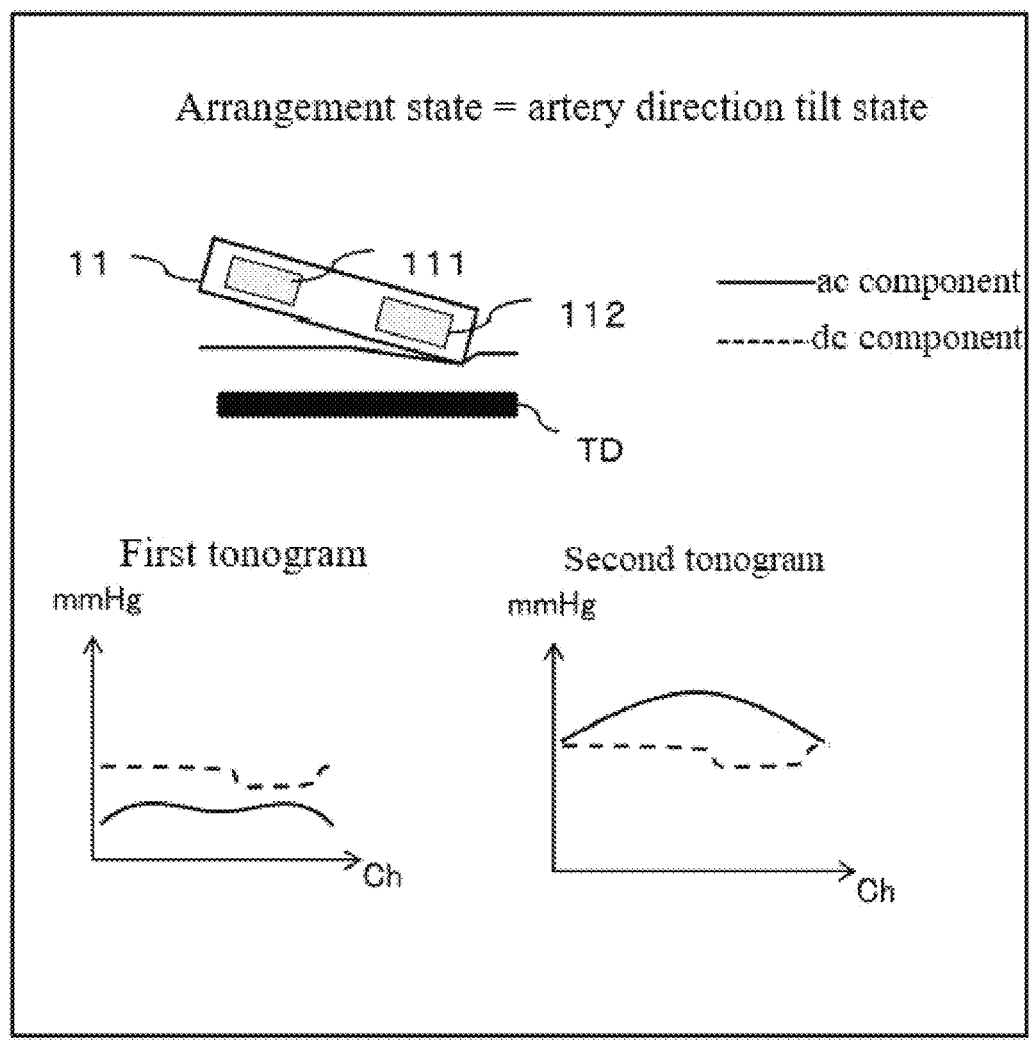
FIG. 12 is a diagram showing an arrangement state in which the sensor unit of the blood pressure measurement apparatus of the first embodiment is tilted in the artery direction, and the shapes of tonograms in this arrangement state.

Also, as shown in FIG. 12, in the case where in either the first tonogram or the second tonogram, the ac component and the dc component both have a flat shape with a low level, and in the other tonogram, the ac component and the dc component both have a flat shape with a high level, it can be inferred that the arrangement state is a state in which the sensor unit 11 is tilted in a direction parallel to the extending direction of the radial artery TD (this tilt direction being called the "artery direction" hereinafter), that is to say an artery direction tilt state.

Figure 13:
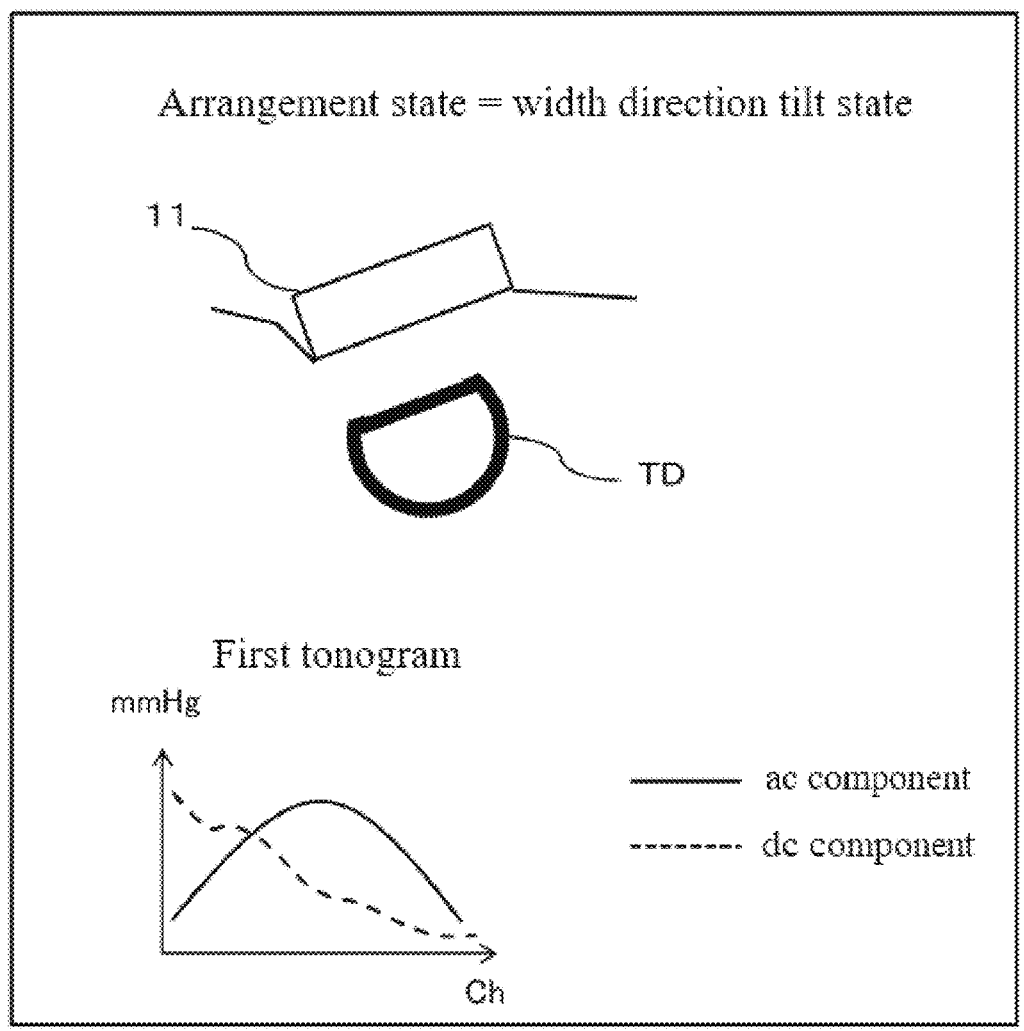
FIG. 13 is a diagram showing an arrangement state in which the sensor unit of the blood pressure measurement apparatus of the first embodiment is tilted in the width direction, and the shapes of tonograms in this arrangement state.

Also, as shown in FIG. 13, in the case where the dc component of the first tonogram is shaped as a line that is inclined in one direction instead of being flat, it can be inferred that the arrangement state is a state in which the sensor unit 11 is tilted in a direction perpendicular to the extending direction of the radial artery TD (this tilt direction being called the "width direction" hereinafter), that is to say a width direction tilt state.

Figure 14:
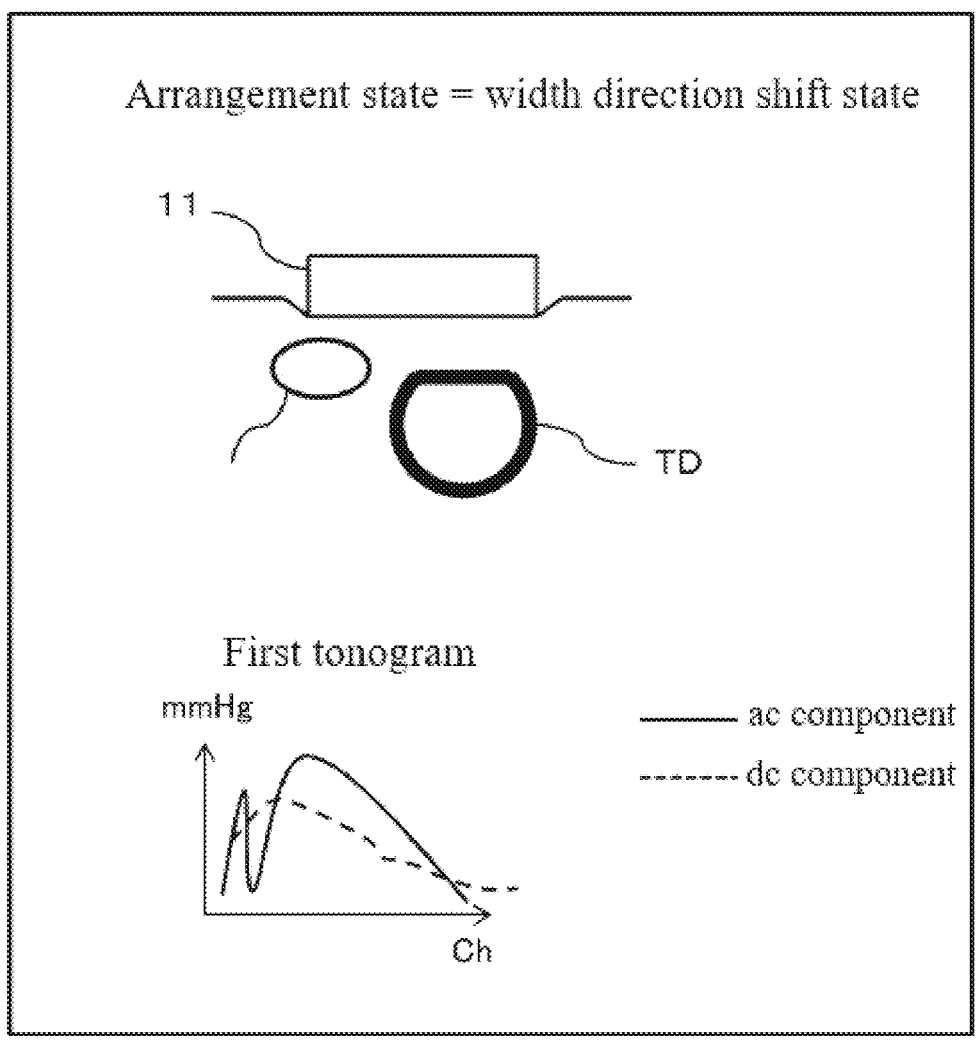
FIG. 14 is a diagram showing an arrangement state in which the sensor unit of the blood pressure measurement apparatus of the first embodiment is shifted in the width direction, and the shapes of tonograms in this arrangement state.

Also, as shown in FIG. 14, in the case where the position of the peak channel in the first tonogram is largely shifted to the left or right of the center, it can be inferred that the arrangement state is a state in which the sensor unit 11 is shifted in the width direction, that is to say a width direction shift state.

Figure 15:
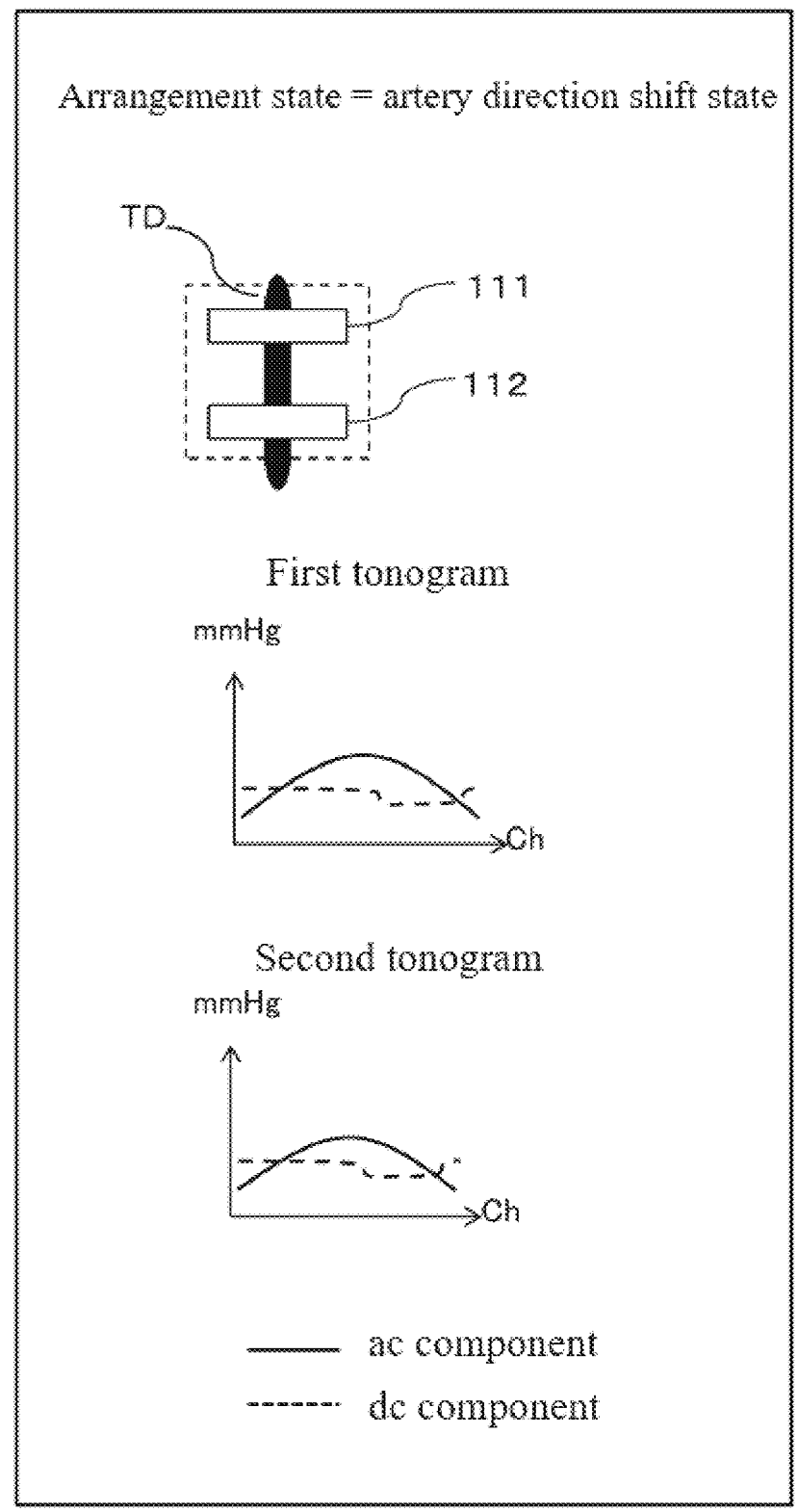
FIG. 15 is a diagram showing an arrangement state in which the sensor unit of the blood pressure measurement apparatus of the first embodiment is shifted in the artery direction, and the shapes of tonograms in this arrangement state.

Also, as shown in FIG. 15, in the case where the difference between the heights of the peak values in the first tonogram and the second tonogram is not very large (the difference between the output values of the peak channels is small), it can be inferred that the arrangement state is a state in which the sensor unit 11 is shifted in the artery direction, that is to say an artery direction shift state.

Figure 16:
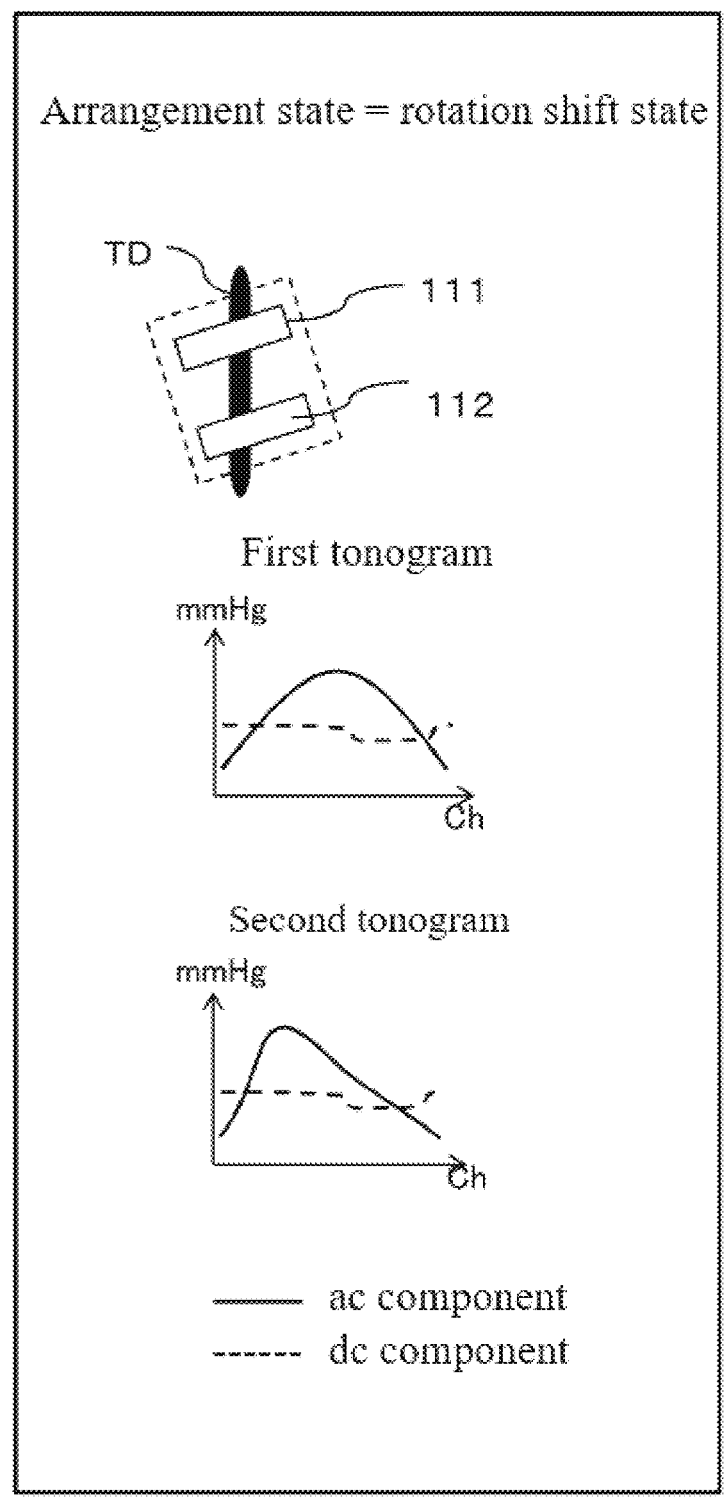
FIG. 16 is a diagram showing an arrangement state in which the sensor unit of the blood pressure measurement apparatus of the first embodiment is shifted in the rotation direction, and the shapes of tonograms in this arrangement state.

Also, as shown in FIG. 16, in the case where the positions of the peak channels are largely shifted between the first tonogram and the second tonogram, it can be inferred that the arrangement state is a state in which the sensor unit 11 is shifted in the rotation direction in the plane of contact with the body surface, that is to say a rotation shift state.

Inference of Arrangement State and Calculation of Reliability

Figure 17:
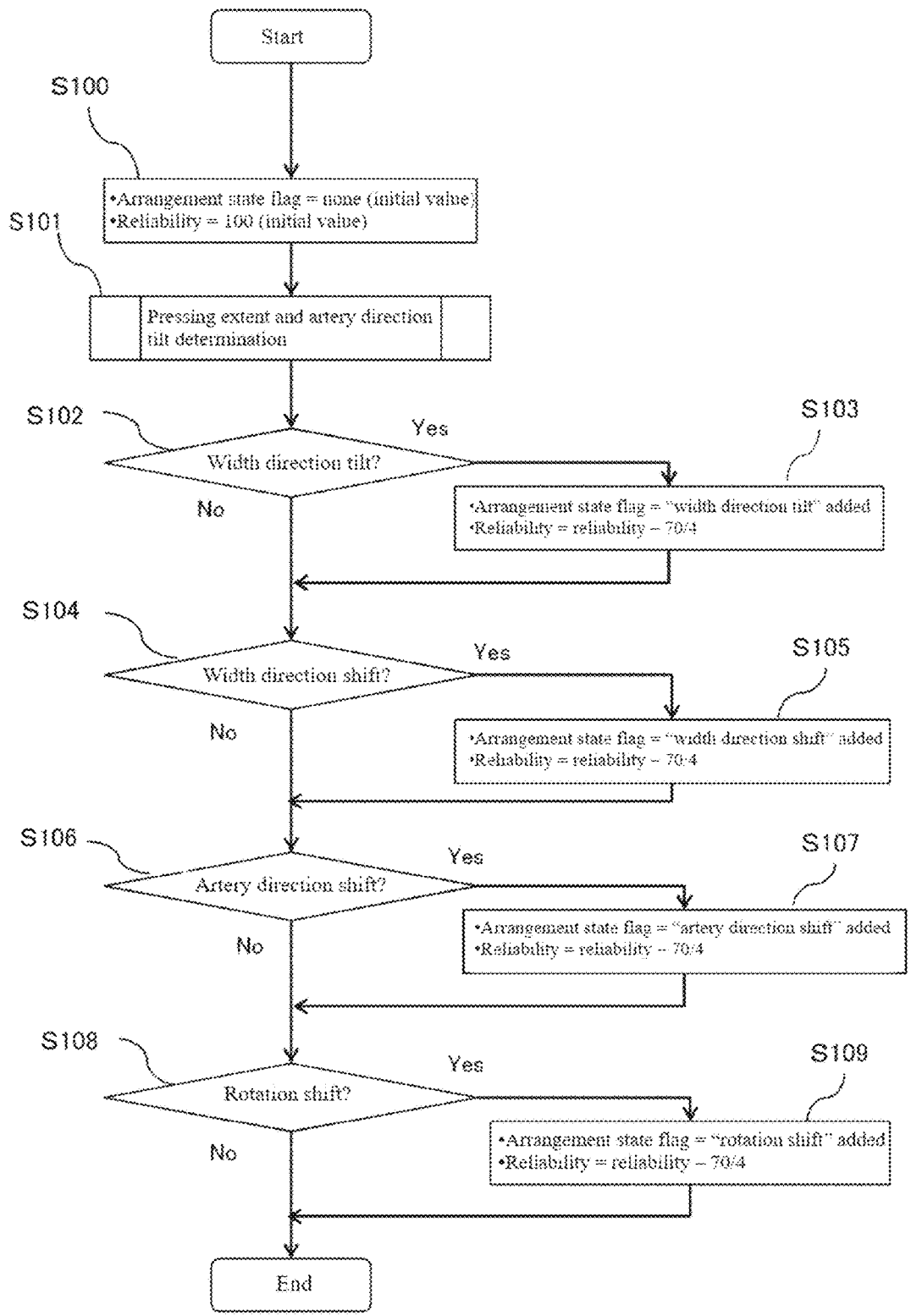
FIG. 17 is a flowchart showing an example of processing performed when an arrangement state inference unit of the blood pressure measurement apparatus of the first embodiment infers the arrangement state of the sensor unit.
Figure 18:
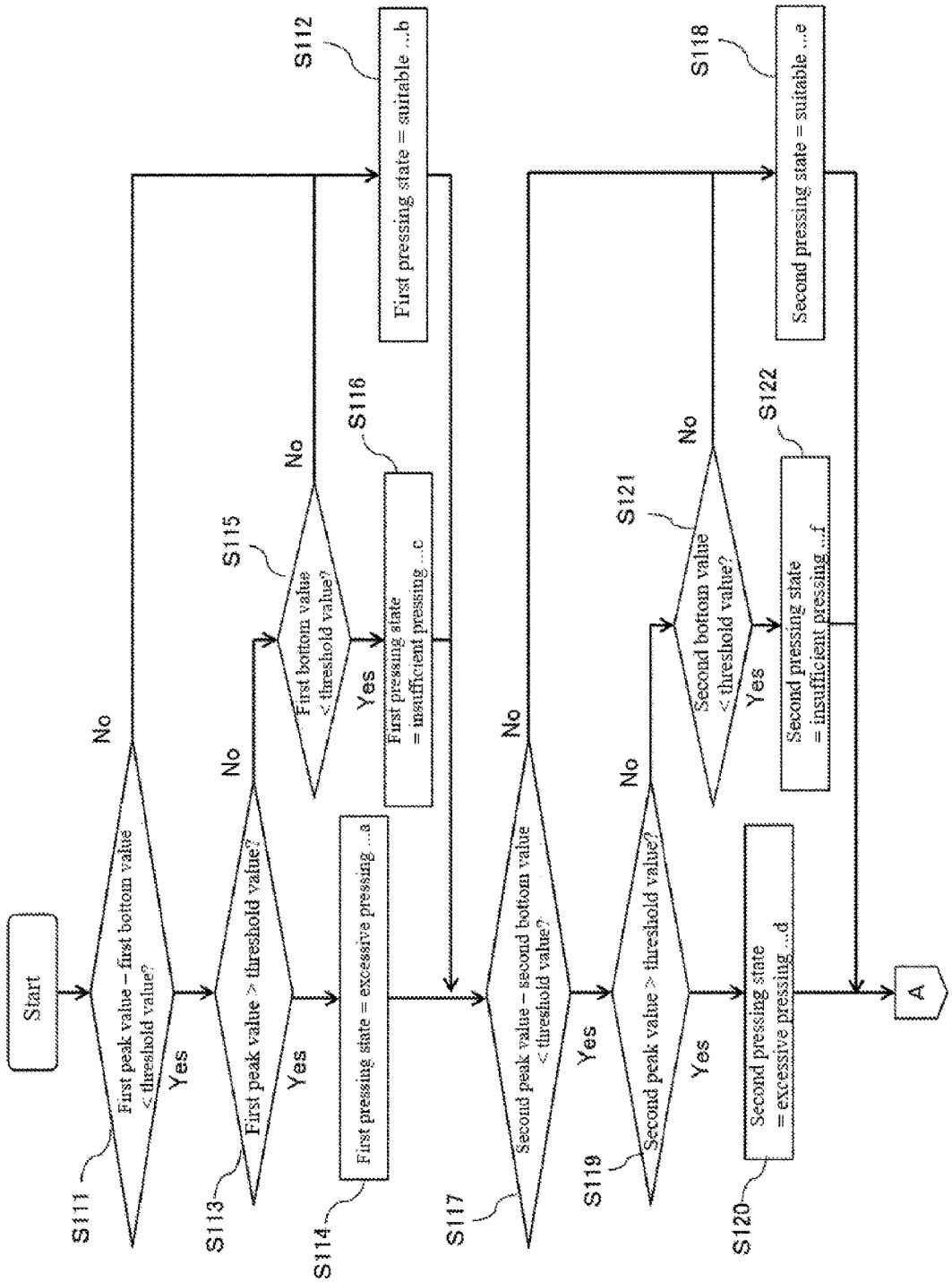
FIG. 18 is part of a flowchart showing an example of processing in the "determine pressing state and artery direction tilt" step in FIG. 17.
Figure 19:
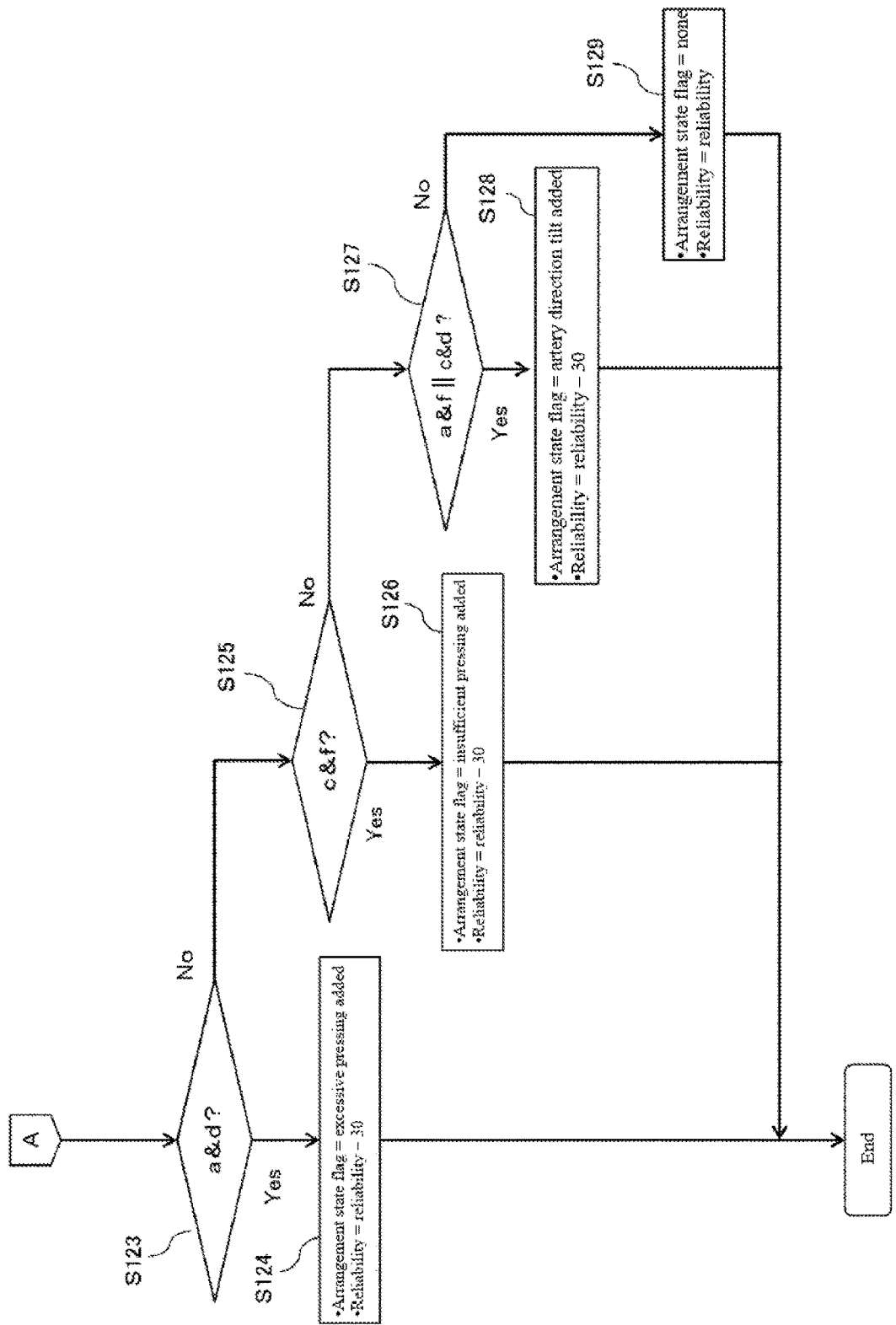
FIG. 19 is another part of a flowchart showing an example of processing in the "determine pressing state and artery direction tilt" step in FIG. 17.

The arrangement state inference unit 23 infers the arrangement state of the sensor unit 11 relative to the radial artery TD based on the feature quantities and/or the shapes of the tonograms, and the reliability calculation unit 24 calculates a reliability according to the arrangement state. FIG. 17 is a flowchart showing an example of processing performed when an arrangement state inference unit 23 infers the arrangement state of the sensor unit 11. FIGS. 18 and 19 are parts of a flowchart showing an example of processing in the "determine pressing state and artery direction tilt" step in FIG. 17, and a single flow is shown in FIGS. 18 and 19. The following describes a method by which the arrangement state inference unit infers an arrangement state, with reference to FIGS. 17, 18, and 19.

The arrangement state inference unit 23 and the reliability calculation unit 24 are respectively set with "arrangement state flag=none (suitable state)" and "reliability=100" as initial values (step S100).

The arrangement state inference unit 23 first makes a determination regarding "pressing extent and artery direction tilt" (step S101). As shown in FIGS. 18 and 19, the arrangement state inference unit 23 infers the extent of pressing of the first sensor array 111, then infers the extent of pressing of the second sensor array 112, and then infers the "pressing state and artery direction tilt" of the sensor unit 11 based on a combination of the extents of pressing of the first sensor array 111 and the second sensor array 112.

Specifically, first, for the first sensor array 111, it is determined whether or not the difference between the first peak value and the first bottom value exceeds a predetermined output value difference threshold value (step S111). Here, if the difference between the first peak value and the first bottom value exceeds the predetermined output value difference threshold value, it is inferred that the extent of pressing of the first sensor array 111 is suitable (step S112).

If the difference between the first peak value and the first bottom value does not exceed the predetermined output value difference threshold value in step S111, it is then determined whether or not the first peak value exceeds a predetermined excessive pressing level threshold value (S113). Here, if the first peak value exceeds the excessive pressing level threshold value, it is inferred that the extent of pressing of the first sensor array 111 is an excessive pressing state (step S114).

If the first peak value does not exceed the excessive pressing level threshold value in step S113, it is then determined whether or not the first bottom value is below a predetermined insufficient pressing level threshold value (S115). Here, if the first bottom value is below the predetermined insufficient pressing level threshold value, it is inferred that the extent of pressing of the first sensor array 111 is an insufficient pressing state (S116), and if it is not below the predetermined insufficient pressing level threshold value, it is inferred that the extent of pressing of the first sensor array 111 is suitable.

Next, for the second sensor array 112 as well, the pressing extent is inferred similarly to the case of the first sensor array 111 (steps S117 to S122).

Subsequently, it is determined whether or not the first sensor array 111 and the second sensor array 112 are both being pressed excessively (step S123). Here, if the excessive pressing state is inferred in both cases, it is inferred that the sensor unit 11 is in the "excessive pressing state" against the radial artery TD, and "excessive pressing state" is added to the arrangement state flag (S124).

If a negative determination is made in step S123 regarding whether or not both the first sensor array 111 and the second sensor array 112 are being pressed excessively, it is determined whether or not both the first sensor array 111 and the second sensor array 112 are being pressed insufficiently (step S125). Here, if it is determined that both the first sensor array 111 and the second sensor array 112 are in the insufficient pressing state, it is inferred that the sensor unit 11 is in the "insufficient pressing state" against the radial artery TD, and "insufficient pressing state" is added to the arrangement state flag (step S126).

If a negative determination is made in step S125 regarding whether or not both the first sensor array 111 and the second sensor array 112 are in the insufficient pressing state, it is determined whether or not either one of the first sensor array 111 and the second sensor array 112 is in the excessive pressing state and the other one is in the insufficient pressing state (step S127). Here, if it is determined that either one of the first sensor array 111 and the second sensor array 112 is in the excessive pressing state and the other one is in the insufficient pressing state, it is inferred that the sensor unit 11 is in the "artery direction tilt state" relative to the radial artery TD, and "artery direction tilt state" is added to the arrangement state flag (step S128).

If a negative determination is made in step S127 regarding whether or not either one of the first sensor array 111 and the second sensor array 112 is in the excessive pressing state and the other one is in the insufficient pressing state, it is inferred that the sensor unit 11 is in the "appropriate arrangement state" relative to the radial artery TD (step S129).

Also, if the arrangement state inferred by the arrangement state inference unit 23 is the "excessive pressing state", the "insufficient pressing state", or the "artery direction tilt state", the reliability calculation unit 24 subtracts 30 from the value of the reliability.

As shown in FIG. 17, the arrangement state inference unit 23 then determines whether or not the sensor unit 11 is tilted in the width direction (step S102). Specifically, a "dc component tilt" is obtained as the difference between the value of the dc component from the pressure sensor 110 located at the channel that is 10 higher than the peak channel in the first sensor array 111, and the value of the dc component from the pressure sensor 110 located at the channel that is 10 lower than the peak channel in the first sensor array 111.

If the above-described dc component tilt value is greater than or equal to a predetermined dc component tilt threshold value, the arrangement state inference unit 23 infers that the sensor unit 11 is in the "width direction tilt state" relative to the radial artery TD, and adds "width direction tilt state" to the arrangement state flag (step S103). The reliability calculation unit 24 also subtracts the value 70/4 from the value of the reliability.

Note that the dc component tilt need only be obtained using values at two or more points in the tonogram, is not necessarily limited to being obtained using the positions of the pressure sensors 110 at the above-described channels, and may be obtained through linear regression performed using the values of all of the channels.

The arrangement state inference unit 23 subsequently determines whether or not the sensor unit 11 is shifted in the width direction (step S104). Specifically, if the channel number of the peak channel in the first sensor array 111 is not within an allowable range for the peak channel position, it is inferred that the sensor unit 11 is in the "width direction shift state" relative to the radial artery TD, and "width direction shift state" is added to the arrangement state flag (step S105). The reliability calculation unit 24 also subtracts the value 70/4 from the value of the reliability.

Here, in the case where the sensor arrays are each constituted by 46 pressure sensors 110 for example, the allowable range for the peak channel position can be a numerical value range of 20 to 26, with 20 as the peak channel lower limit threshold value, and 26 as the peak channel upper limit threshold value.

Note that the method of determining whether or not the sensor unit is shifted in the width direction is not limited to the above description, and it is also possible to infer that the arrangement state is the width direction shift state if the ac component of a tonogram has multiple peaks for example, that is to say if there are two or more local maximum values in the ac component.

The arrangement state inference unit 23 subsequently determines whether or not the sensor unit 11 is shifted in the artery direction (step S106). Specifically, if the difference between the peak value of the first sensor array 111 and the peak value of the second sensor array 112 is below the predetermined peak value difference threshold value, it is inferred that the sensor unit 11 is in the "artery direction shift state" relative to the radial artery TD, and "artery direction shift state" is added to the arrangement state flag (step S107). The reliability calculation unit 24 also subtracts the value 70/4 from the value of the reliability.

The arrangement state inference unit 23 subsequently determines whether or not the sensor unit 11 is shifted in the rotation direction (step S108). Specifically, if the difference between the peak channel number of the first sensor array 111 and the peak channel number of the second sensor array 112 exceeds a predetermined peak channel difference threshold value, it is inferred that the sensor unit 11 is in the "rotation shift state" relative to the radial artery TD, and "rotation shift state" is added to the arrangement state flag (step S109). The reliability calculation unit 24 also subtracts the value 70/4 from the value of the reliability.

As described above, it is finally inferred that the arrangement state of the sensor unit 11 relative to the radial artery TD is one of 64 patterns, the reliability of the measurement value is calculated in accordance with the inferred arrangement state, and the calculated reliability is recorded in the storage unit 40 along with the measured blood pressure information and the specified blood pressure indices.

Effects of Blood Pressure Measurement Apparatus of Present Embodiment

According to the configuration described above, the blood pressure measurement apparatus 1 of the present embodiment can efficiently infer the arrangement state of the sensor unit 11 from the viewpoint of pressing extent, artery direction tilt, width direction tilt, artery direction shift, width direction shift, and rotation shift. Also, based on the arrangement state of the sensor unit 11 inferred in this way, it is possible to obtain the reliability of blood pressure information measured by the sensor unit 11 on a scale of 100 points. For this reason, blood pressure information obtained when the sensor unit 11 is in an unsuitable arrangement state (i.e., a measurement value having a low reliability) can be prevented from being treated similarly to blood pressure information obtained when the sensor unit 11 is in a suitable arrangement state (i.e., a measurement value having a high reliability).

Variations

Note that although reliability value calculation is performed in five steps for arrangement state inference in the present embodiment, it is not necessarily required that this method is employed, and the reliability may be calculated based on the finally inferred arrangement state.

Also, although the "pressing extent and artery direction tilt" state is set with a value that has a larger influence on the reliability than the other unsuitable arrangement states (30 for the former, and 70/4 for the latter) in the present embodiment, it is not necessarily required that the values are set in this way.

Furthermore, although the reliability is calculated on a scale of 100 points in the present embodiment, it is not necessarily required to be such a scale of continuous values, and the reliability may be expressed by evaluation grades such as "reliable", "somewhat reliable", "not very reliable", "hardly reliable", and "not reliable at all".

Also, although it is finally inferred that the arrangement state is one of 64 patterns in the present embodiment, there is no limitation to this, and the arrangement state may be inferred from a larger number of patterns. For example, although only "yes and no" are inferred for shift and tilt in the present embodiment, it is possible to add the element of "in which direction" when shift or tilt is occurring, such that the final arrangement state is inferred from among 729 patterns of arrangement states. Furthermore, it is possible to add the element "to what extent", and infer the arrangement state in finer detail.

Also, conversely, arrangement state inference may be performed using a smaller number of determination elements. For example, the final arrangement state may be inferred based on only "pressing extent", "presence/absence of width direction shift", and "presence/absence of width direction tilt". In such a case, the arrangement state can be inferred using simply one sensor array.

Also, the information that is recorded to the storage unit 40 is not limited to the information described in the present embodiment, and it is possible to additionally record data indicating the tonograms created by the tonogram creation unit 22 and information indicating the arrangement state inferred by the arrangement state inference unit 23.

Second Embodiment

Hereinafter, a second embodiment of the present invention will be described with reference to FIGS. 20 to 23. Note that the hardware configuration of the present embodiment is substantially the same as that of the first embodiment, with the exception of having an output unit 50, and therefore like portions are given the same reference signs as in the first embodiment, and will not be described in detail. Also, the processing performed by the blood pressure measurement apparatus and the functions of the control unit 20 are also largely the same as in the first embodiment, and therefore detailed descriptions will not be given for such portions.

Configuration of Blood Pressure Measurement Apparatus

Figure 20:
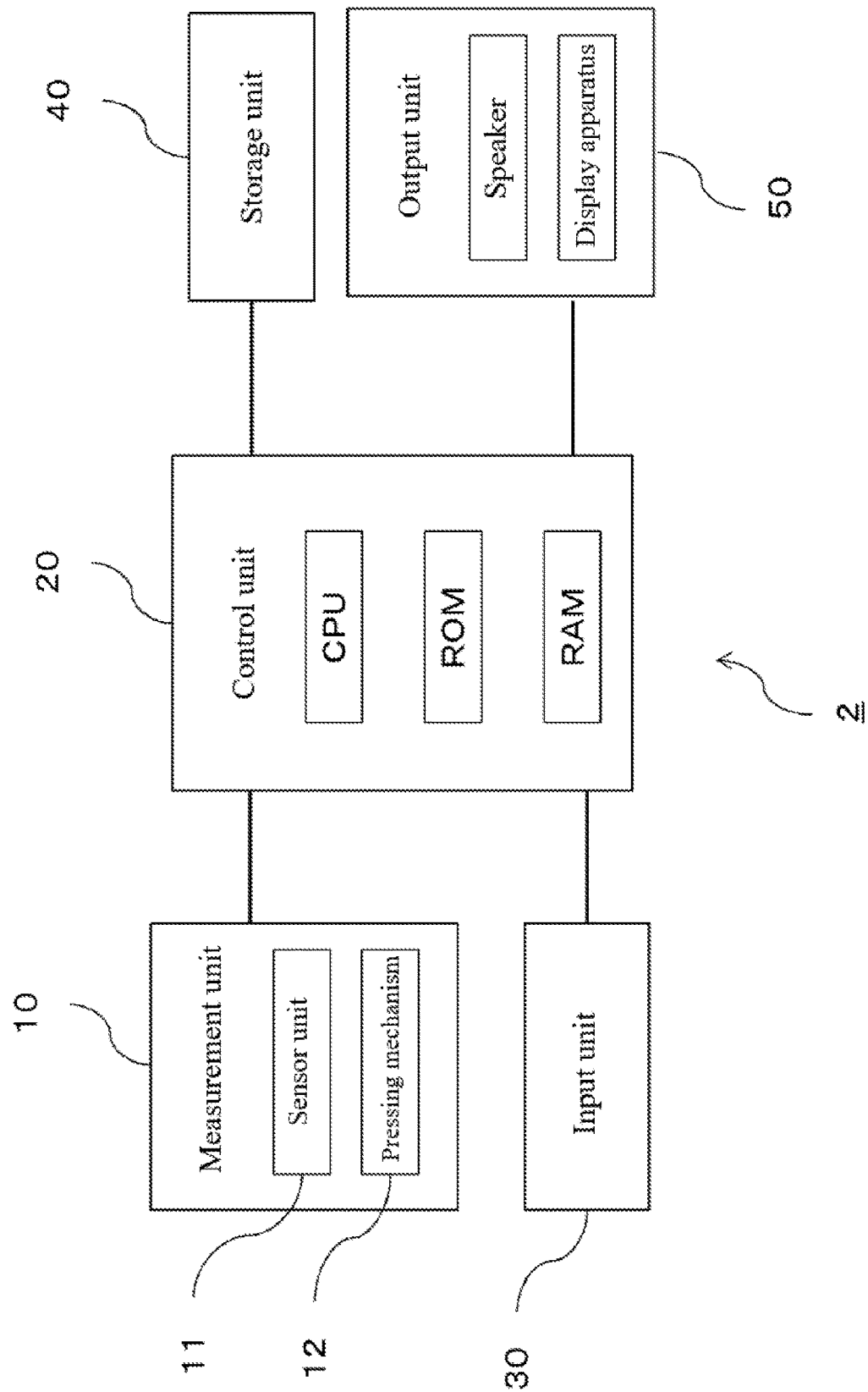
FIG. 20 is a block diagram showing an overall configuration of a blood pressure measurement apparatus according to a second embodiment of the present invention.

FIG. 20 is a block diagram showing the overall configuration of a blood pressure measurement apparatus 2 of the present embodiment. The blood pressure measurement apparatus 2 mainly has the measurement unit 10, the control unit 20, the input unit 30, the storage unit 40, and an output unit 50. As previously mentioned, with the exception of the output unit 50, the configurations and functions are similar to those in the first embodiment.

The output unit 50 provides the user with interfaces for outputting information. In the present embodiment, it is presumed that the output unit 50 has a liquid crystal display and a speaker, but the present invention is not necessarily limited to this. For example, it is also possible to use a display apparatus other than a liquid crystal display, an audio output device other than a speaker, a communication apparatus that performs data communication with another device, and the like. The data communication performed in the communication apparatus may be performed via a wire or wirelessly. A combination of the above is also possible.

Functions of Control Unit

Figure 21:
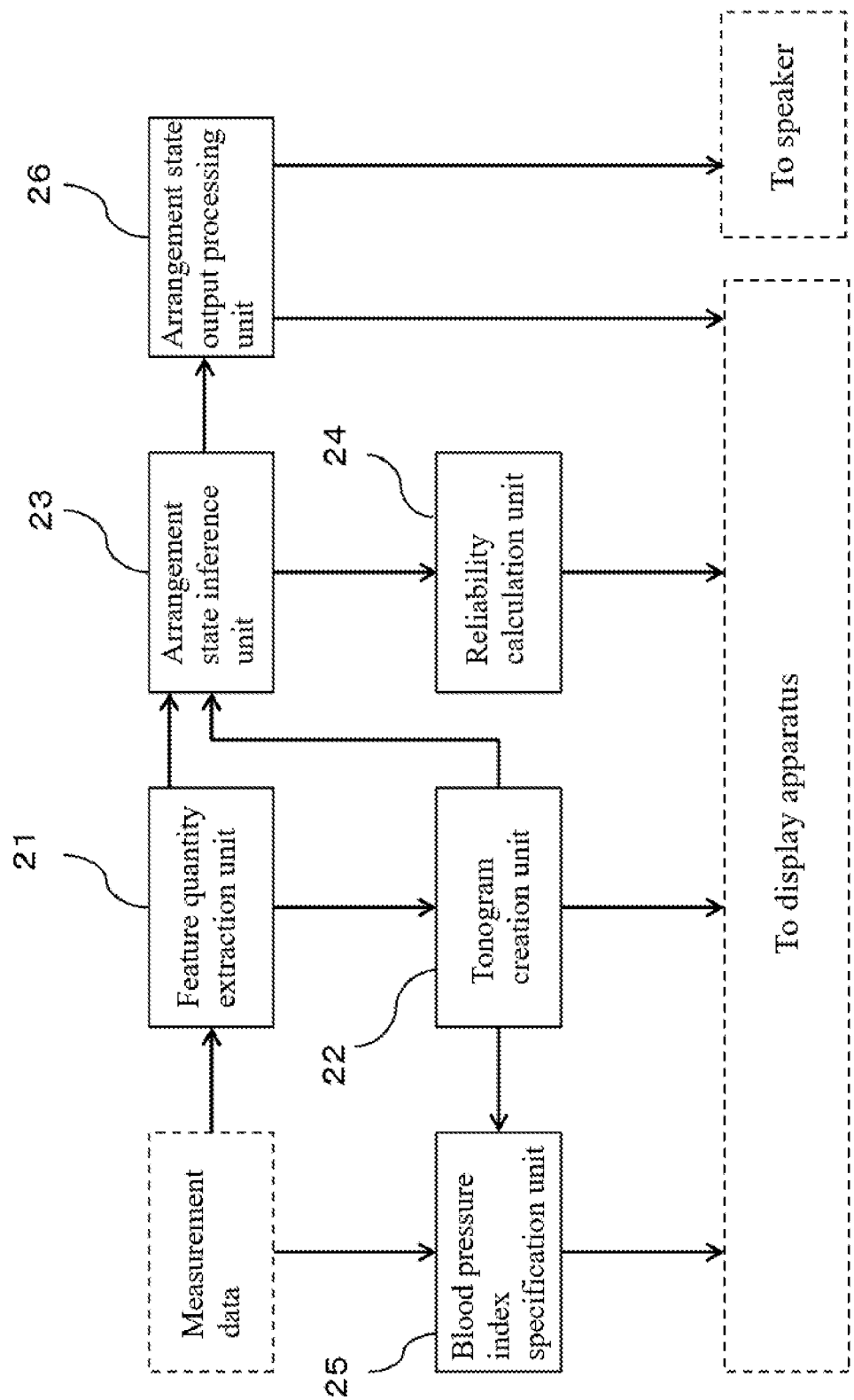
FIG. 21 is a block diagram showing an overview of a functional configuration of a control unit of the blood pressure measurement apparatus of the second embodiment.

FIG. 21 is a block diagram showing an overview of the functional configuration of the control unit 20. As shown in FIG. 21, as basic functions, the control unit 20 has the feature quantity extraction unit 21, the tonogram creation unit 22, the arrangement state inference unit 23, the reliability calculation unit 24, the blood pressure index specification unit 25, and an arrangement state output processing unit 26. In the present embodiment, the functions of these units are realized by the control unit 20 executing necessary programs. The configurations other than the arrangement state output processing unit 26 are similar to those in the first embodiment.

The arrangement state output processing unit 26 is a function for performing processing according to which the later-described output unit 50 performs output that corresponds to the inferred arrangement state of the sensor unit 11.

Functions of Blood Pressure Measurement Apparatus

Figure 22:
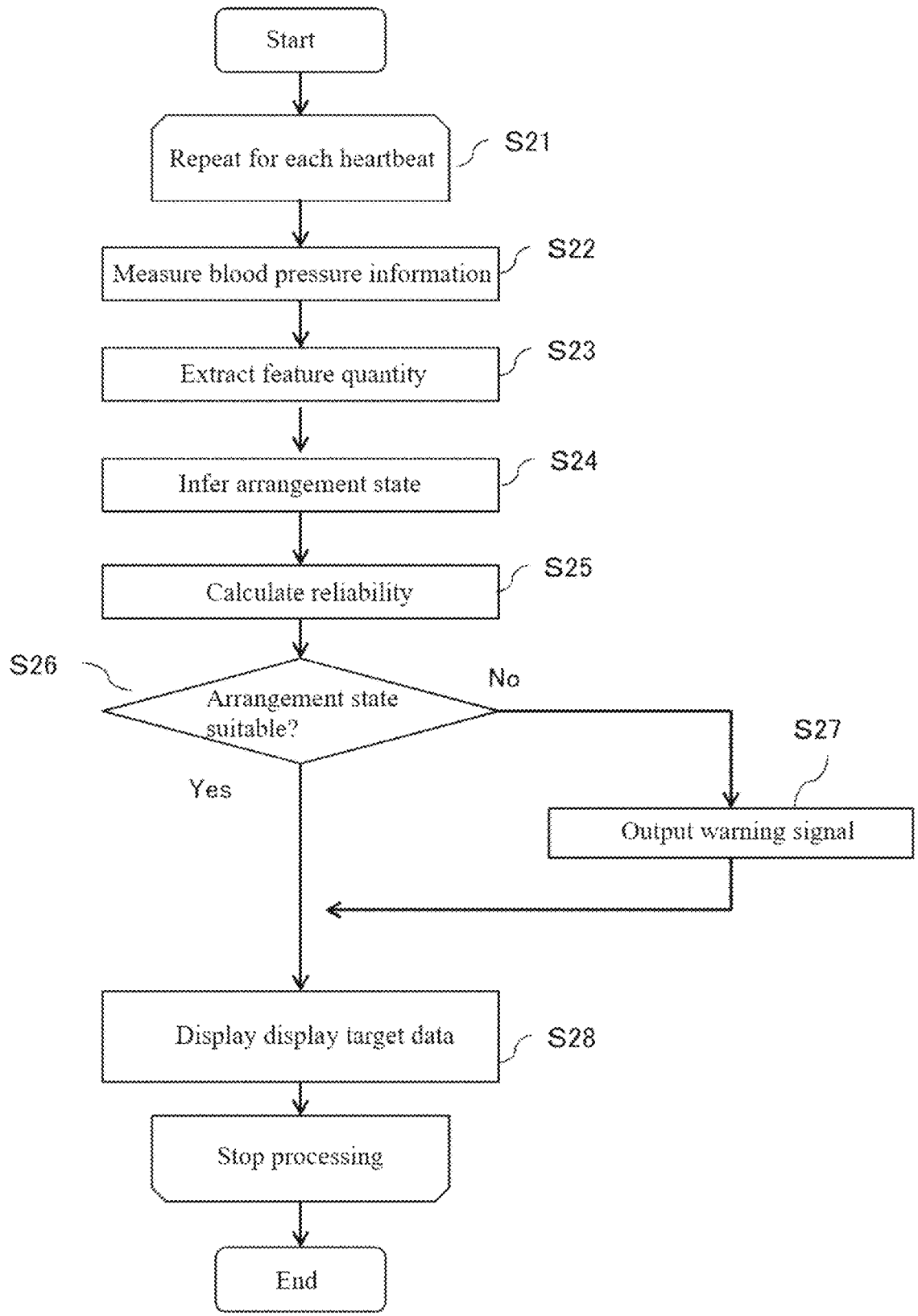
FIG. 22 is a flowchart showing an example of the overall flow of processing performed by the blood pressure measurement apparatus of the second embodiment.

FIG. 22 is a flowchart showing an example of the overall flow of processing performed by the blood pressure measurement apparatus 2 of the present embodiment. As shown in FIG. 22, for each heartbeat, the blood pressure measurement apparatus 2 measures blood pressure information (step S22), extracts feature quantities from the measured information and creates a tonogram (step S23), infers the arrangement state of the sensor unit 11 relative to the radial artery TD based on the tonogram (step S24), and calculates a reliability based on the inferred arrangement state (step S25). The flow up to this point is similar to that in the first embodiment.

The blood pressure measurement apparatus 2 further determines whether or not the inferred arrangement state of the sensor unit 11 is "suitable" (step S26), and upon determining that it is not "suitable", outputs a warning signal from the output unit 50 (step S27).

Thereafter, the blood pressure measurement apparatus displays, on a display unit, the blood pressure indices that were specified by the blood pressure index specification unit 25, an illustration of the estimated arrangement state of the sensor unit 11, the calculated reliability, and a comment corresponding to the inferred arrangement state (step S28).

Blood pressure information measurement, feature quantity extraction, arrangement state inference, and reliability calculation are similar to that in the first embodiment, and therefore will not be described, and the following describes processing that the arrangement state output processing unit 26 performs based on the inferred arrangement state.

The arrangement state output processing unit 26 first determines whether or not the inferred arrangement state is "suitable", and if it is not "suitable", performs processing such that a warning sound based on a warning signal is emitted from a speaker. Note that the case where the arrangement state is not suitable refers to the case where the reliability of the measured blood pressure information is less than or equal to a predetermined value, and therefore the determination of whether or not to emit the warning signal may be made based on whether or not the value of the reliability exceeds the predetermined value.

Here, the sound may be one type of warning sound, or may be various types of warning sounds that correspond to different arrangement states. Also, a warning corresponding to the arrangement state may be given using a language-based voice message. In this case, the voice data may be obtained by selecting corresponding voice data from a voice database in the storage unit 40.

Also, the arrangement state output processing unit 26 performs processing for displaying, on the display unit, an "arrangement state illustration image" that corresponds to the inferred arrangement state. Here, the arrangement state illustration image may be acquired by selecting corresponding arrangement state illustration image data from an arrangement state illustration image database in the storage unit 40.

Furthermore, the arrangement state output processing unit 26 performs processing for displaying, on the display unit, an "arrangement state comment" that corresponds to the inferred arrangement state. Also, the arrangement state comment for the case where the arrangement state is not "suitable" may be displayed along with a "correction instruction comment" that indicates how the arrangement state is to be corrected so as to become suitable. Here, the arrangement state comment and the correction instruction comment may be acquired by selecting data from a database in the storage unit 40. In this case, it is possible to prepare comment data in which a correction comment is included in the arrangement state comment, and an arrangement state comment and a correction comment may be stored separately in the database.

Display of Information on Display Apparatus

Figure 23A:
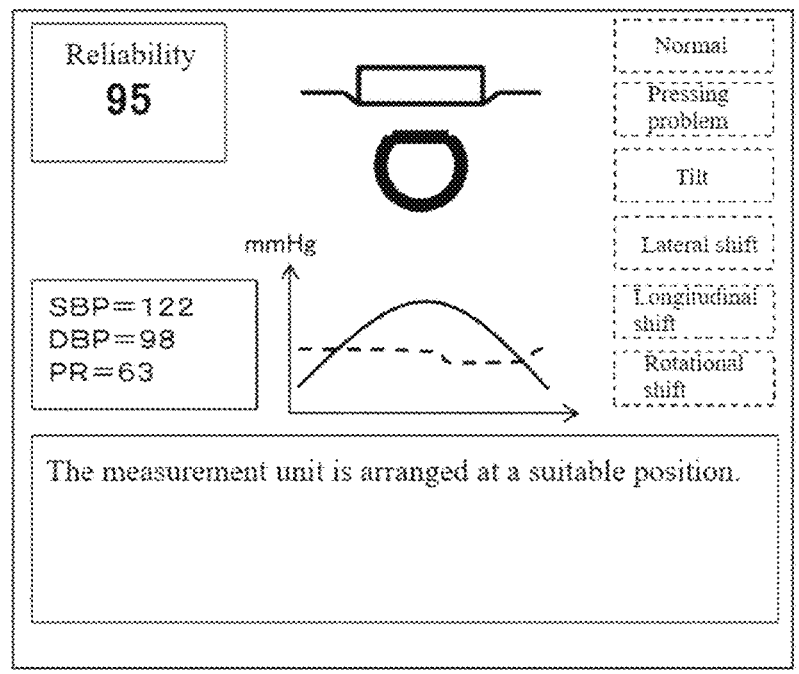
FIGS. 23A and 23B are diagrams showing examples of images displayed by an output unit of the blood pressure measurement apparatus of the second embodiment.
Figure 23B:
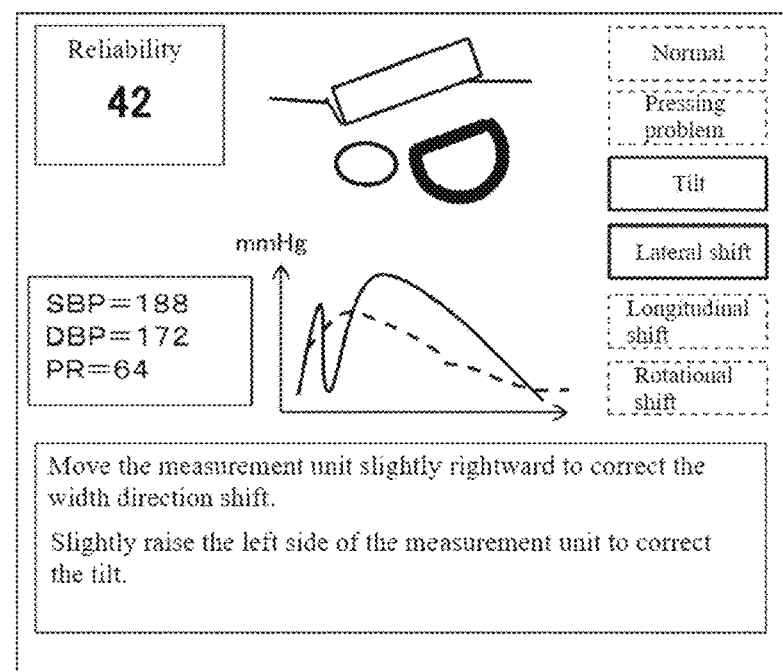

Along with the information obtained by the above-described processing of the arrangement state output processing unit 26, the control unit 20 displays, on a liquid crystal display, the first tonogram created by the tonogram creation unit 22, the reliability calculated by the reliability calculation unit 24, and the blood pressure indices specified by the blood pressure index specification unit 25. FIGS. 23A and 23B show examples of such a display screen. FIG. 23A shows an example of the case where the sensor unit 11 is in a suitable arrangement state relative to the radial artery TD, and FIG. 23B shows an example of the case where the sensor unit 11 is shifted and tilted in the width direction.

Effects of Blood Pressure Measurement Apparatus of Present Embodiment

According to the configuration described above, through the display on the liquid crystal display, the user of the blood pressure measurement apparatus 2 of the present embodiment can find out, in a more timely manner, the measured blood pressure indices (SBP, DBP, and PR) and the reliability of these blood pressure indices. Also, through the display of the illustration image and text information, it is possible to find out, in a more timely manner, the arrangement state of the sensor unit 11 relative to the radial artery TD that is the measurement target.

Also, in the case where the reliability of the blood pressure information, which includes the blood pressure indices, is less than or equal to a predetermined reference value, the user of the blood pressure measurement apparatus 2 of the present embodiment can immediately find out that fact through audio and/or a display screen. Furthermore, an unsuitable arrangement state that causes a reduction in reliability can be found out in a more timely manner through an illustration image and text information, and a method for putting the sensor unit 11 in a suitable arrangement state can be found out through the display of text information. For this reason, the user can, on their own, correct the arrangement state of the sensor unit 11 to a state that is suited to blood pressure measurement.

Variations

Instead of various types of information merely being displayed on the display, it may be recorded in the storage unit 40 when necessary. Also, there is no limitation to only the displayed information, and a configuration is possible in which all of the measured blood pressure information, second tonogram data, and the like are also recorded.

Also, although information is displayed on a liquid crystal display that is integrated with the blood pressure measurement apparatus in the present embodiment, the information may be transmitted via a communication apparatus and displayed by a monitor that is separate from the blood pressure measurement apparatus, or by a projector or a mobile information terminal such as a smartphone.

Also, although sound is output as the warning signal in the present embodiment, there is no limitation to this, and a warning may be given by the blinking of a light, for example. In such a case, this may performed by the screen of the liquid crystal display, or may be performed using an LED or the like that is separate from the display.

REFERENCE SIGNS LIST 1, 2 blood pressure measurement apparatus
10 measurement unit
11 sensor unit
12 pressing mechanism
110 pressure sensor
111 first sensor array
112 second sensor array
20 control unit
21 feature quantity extraction unit
22 tonogram creation unit
23 arrangement state inference unit
24 reliability calculation unit
25 blood pressure index specification unit
26 arrangement state output processing unit
30 input unit
40 storage unit
50 output unit
TD radial artery

The invention claimed is:

1. A blood pressure measurement apparatus that measures a blood pressure by tonometry, the blood pressure measurement apparatus comprising:
a measurement device that includes a plurality of pressure sensors that measure blood pressure information for each heartbeat in a measurement target; and
a processor configured to:
extract feature quantities from an output waveform of each of the pressure sensors for each heartbeat, and infer an arrangement state of the measurement device relative to an artery that is the measurement target based on a distribution profile of values of the feature quantities for the plurality of pressure sensors; and
calculate a reliability of the blood pressure information measured by the measurement device, based on the inferred arrangement state,
wherein the processor is configured to extract, from the output waveform of each of the pressure sensors for each heartbeat, a difference value between a maximum value and a minimum value in the output waveform, and the minimum value, as the feature quantities, and infer the arrangement state of the measurement device based on a distribution profile of the difference values for the plurality of pressure sensors and a distribution profile of the minimum values,
wherein the measurement device has at least one sensor array that includes at least a portion of the plurality of pressure sensors arranged side-by-side in a direction that intersects the artery during measurement,
wherein the arrangement state includes a pressing extent that indicates an extent of force that the sensor array applies to the artery, and
the processor is configured to infer the pressing extent based on a difference between a peak value and a bottom value in the distribution profile of the difference values and/or the peak value in the distribution profile of the difference values.

2. The blood pressure measurement apparatus according to claim 1,
wherein the at least one sensor array includes a first sensor array including a portion of the plurality of pressure sensors and a second sensor array including another portion of the plurality of pressure sensors, the first sensor array and the second sensor array being arranged parallel with each other,
the arrangement state includes an artery direction tilt that indicates tilt in a direction parallel to a direction of extension of the artery, relative to a reference state that is an orientation suited to measurement, and
the processor is configured to infer the artery direction tilt based on a difference between a peak value and a bottom value in the distribution profile of the difference values and the peak value in the distribution profile of the difference values for each of the first sensor array and the second sensor array.

3. The blood pressure measurement apparatus according to claim 1,
wherein the at least one sensor array includes a first sensor array including a portion of the plurality of pressure sensors and a second sensor array including another portion of the plurality of pressure sensors, the first sensor array and the second sensor array being arranged parallel with each other,
the arrangement state includes an artery direction shift that indicates shift in a direction parallel to a direction of extension of the artery, relative to a reference state that is an orientation suited to measurement, and the processor is configured to infer the artery direction shift based on a difference between peak values in the distribution profiles of the difference values of the first sensor array and the second sensor array.

4. The blood pressure measurement apparatus according to claim 1, wherein the at least one sensor array includes a first sensor array including a portion of the plurality of pressure sensors and a second sensor array including another portion of the plurality of pressure sensors, the first sensor array and the second sensor array being arranged parallel with each other, the arrangement state includes a rotation shift that indicates rotation of the measurement device in a plane of contact with the measurement target, relative to a reference state that is an orientation suited to measurement, and the processor is configured to infer the rotation shift based on a difference between positions of peaks in the distribution profiles of the difference values of the first sensor array and the second sensor array.

5. The blood pressure measurement apparatus according to claim 1, wherein the processor is further configured to output one of or a combination of the blood pressure information, the arrangement state, and the reliability.

6. The blood pressure measurement apparatus according to claim 5, further comprising one of or a combination of a display that outputs one of or a combination of the blood pressure information, the arrangement state, and the reliability, using text and/or an image, a speaker that outputs one of or a combination of the blood pressure information, the arrangement state, and the reliability, using sound, and a communication device that outputs, to another apparatus, one of or a combination of the blood pressure information, the arrangement state, and the reliability, using wired or wireless communication.

7. The blood pressure measurement apparatus according to claim 5, wherein the processor is further configured to output information indicating an unsuitable arrangement state that causes a decrease in the reliability, in a case where the reliability is less than or equal to a predetermined reference value.

8. The blood pressure measurement apparatus according to claim 5, wherein the processor is further configured to output a method of correcting an unsuitable arrangement state that causes a decrease in the reliability to a suitable arrangement state, in a case where the reliability is less than or equal to a predetermined reference value.

9. The blood pressure measurement apparatus according to claim 1, wherein the blood pressure measurement apparatus is a wearable apparatus for being attached to a wrist.

10. A blood pressure measurement apparatus that measures a blood pressure by tonometry, the blood pressure measurement apparatus comprising:

a measurement device that includes a plurality of pressure sensors that measure blood pressure information for each heartbeat in a measurement target; and a processor configured to:

extract feature quantities from an output waveform of each of the pressure sensors for each heartbeat, and infer an arrangement state of the measurement device relative to an artery that is the measurement target based on a distribution profile of values of the feature quantities for the plurality of pressure sensors; and calculate a reliability of the blood pressure information measured by the measurement device, based on the inferred arrangement state, wherein the processor is configured to extract, from the output waveform of each of the pressure sensors for each heartbeat, a difference value between a maximum value and a minimum value in the output waveform, and the minimum value, as the feature quantities, and infer the arrangement state of the measurement device based on a distribution profile of the difference values for the plurality of pressure sensors and a distribution profile of the minimum values, wherein the measurement device has at least one sensor array that includes at least a portion of the plurality of pressure sensors arranged side-by-side in a direction that intersects the artery during measurement, wherein the arrangement state includes a width direction tilt that indicates tilt in a direction perpendicular to a direction of extension of the artery, relative to a reference state that is an orientation suited to measurement, and the processor is configured to infer the width direction tilt based on an inclination in the distribution profile of the minimum values.

11. A blood pressure measurement apparatus that measures a blood pressure by tonometry, the blood pressure measurement apparatus comprising:

a measurement device that includes a plurality of pressure sensors that measure blood pressure information for each heartbeat in a measurement target; and a processor configured to:

extract feature quantities from an output waveform of each of the pressure sensors for each heartbeat, and infer an arrangement state of the measurement device relative to an artery that is the measurement target based on a distribution profile of values of the feature quantities for the plurality of pressure sensors; and calculate a reliability of the blood pressure information measured by the measurement device, based on the inferred arrangement state, wherein the processor is configured to extract, from the output waveform of each of the pressure sensors for each heartbeat, a difference value between a maximum value and a minimum value in the output waveform, and the minimum value, as the feature quantities, and infer the arrangement state of the measurement device based on a distribution profile of the difference values for the plurality of pressure sensors and a distribution profile of the minimum values, wherein the measurement device has at least one sensor array that includes at least a portion of the plurality of pressure sensors arranged side-by-side in a direction that intersects the artery during measurement, wherein the arrangement state includes a width direction shift that indicates shift in a direction perpendicular to a direction of extension of the artery, relative to a reference state that is an orientation suited to measurement, and the processor is configured to infer the width direction shift based on a position of a peak in the distribution profile of the difference values.

12. A method of controlling a blood pressure measurement apparatus that measures a blood pressure by tonometry, the method comprising:
- a measuring step of, with use of a measurement device that includes a plurality of pressure sensors, measuring blood pressure information for each heartbeat in a measurement target;
- a step of extracting feature quantities from an output waveform of each of the pressure sensors for each heartbeat;
- a step of inferring an arrangement state of the measurement device relative to an artery that is the measurement target based on a distribution profile of values of the feature quantities for the plurality of pressure sensors; and
- a step of calculating a reliability of the blood pressure information measured by the measurement device, based on the inferred arrangement state,
- wherein the extracting comprises extracting, from the output waveform of each of the pressure sensors for each heartbeat, a difference value between a maximum value and a minimum value in the output waveform, and the minimum value, as the feature quantities, and
- wherein the inferring comprises inferring the arrangement state of the measurement device based on a distribution profile of the difference values for the plurality of pressure sensors and a distribution profile of the minimum values,
- wherein the measurement device has at least one sensor array that includes at least a portion of the plurality of pressure sensors arranged side-by-side in a direction that intersects the artery during measurement,
- wherein the arrangement state includes a pressing extent that indicates an extent of force that the sensor array applies to the artery, and
- wherein the inferring comprises inferring the pressing extent based on a difference between a peak value and a bottom value in the distribution profile of the difference values and/or the peak value in the distribution profile of the difference values.

13. A non-transitory computer readable storage medium having stored thereon a program for causing the steps of the method of controlling a blood pressure measurement apparatus according to claim 12 to be executed by the blood pressure measurement apparatus.

\* \* \* \* \*